United States Patent
Wowk et al.

(10) Patent No.: US 7,278,278 B2
(45) Date of Patent: Oct. 9, 2007

(54) CRYOGENIC STORAGE SYSTEM

(75) Inventors: Brian Wowk, Corona, CA (US);
Michael Iarocci, Patchogue, NY (US)

(73) Assignee: 21st Century Medicine, Inc., Rancho Cucamonga, CA (US)

( * ) Notice: Subject to any disclaimer, the term of this patent is extended or adjusted under 35 U.S.C. 154(b) by 298 days.

(21) Appl. No.: 10/864,921

(22) Filed: Jun. 9, 2004

(65) Prior Publication Data

US 2005/0016198 A1 Jan. 27, 2005

Related U.S. Application Data

(60) Provisional application No. 60/478,674, filed on Jun. 12, 2003.

(51) Int. Cl.
*F25D 3/08* (2006.01)

(52) U.S. Cl. .......................................... 62/371; 62/45.1

(58) Field of Classification Search .................. 62/371, 62/373, 457.2, 457.9, 45.1, 48.3
See application file for complete search history.

(56) References Cited

U.S. PATENT DOCUMENTS

| | | | |
|---|---|---|---|
| 3,729,946 A * | 5/1973 | Massey | ....................... 62/50.1 |
| 4,495,782 A * | 1/1985 | Salour et al. | ................. 62/51.1 |
| 4,559,298 A | 12/1985 | Fahy | |
| 4,848,093 A * | 7/1989 | Simmonds et al. | ........... 62/49.1 |
| 5,174,122 A * | 12/1992 | Levine | ........................ 62/50.2 |
| 5,217,860 A | 6/1993 | Fahy et al. | |
| 6,167,710 B1 * | 1/2001 | Cosman | .......................... 62/78 |

OTHER PUBLICATIONS

Fahy, et al., "Physical problems with the vitrification of large biological systems," *Cryobiology* 27:492-510 (1990).
Baudot, et al., "Physical Vitrification of Rabbit Aortas without any Fracture," *Cryobiology* 43:375-376 (2001).

* cited by examiner

*Primary Examiner*—Melvin Jones
(74) *Attorney, Agent, or Firm*—Foley & Lardner LLP; Stephen E. Reiter

(57) ABSTRACT

The present invention provides devices and methods for the cryogenic storage of biological material. Devices of the invention are useful for storing material at a cryogenic temperature. The devices include a temperature chamber defined by a thermally-conductive container and at least one layer of thermal insulation surrounding the thermally-conductive container. Some embodiments utilize one or more heat sources thermally connected to the thermally conductive container. Other embodiments are arranged so that no net flow of heat occurs from the temperature chamber when the temperature chamber is at a set target temperature. Also provided are methods of using the devices.

32 Claims, 16 Drawing Sheets

CRYOGENIC STORAGE SYSTEM

This application claims the benefit of U.S. application Ser. No. 60/478,674, filed Jun. 12, 2003, which is hereby incorporated by reference in its entirety, including all Figures, Table, and Claims.

FIELD OF THE INVENTION

The present invention relates to the field of cryogenic storage systems.

BACKGROUND OF THE INVENTION

The following discussion of the background of the invention is merely provided to aid the reader in understanding the invention and is not admitted to describe or constitute prior art to the present invention.

Stable storage for long periods of time typically requires cold temperatures. This is especially true for biological tissue. Water located between ice crystals contains concentrated solutes, and therefore remains a viscous fluid until the glass transition temperature is reached. At the glass transition temperature a crystal-free immobilized liquid state known as a "glass" is formed. This typically occurs between −80° C. and −130° C. Below the glass transition temperature, translational molecular motion and chemical conversions are arrested, and storage for indefinite periods of time becomes possible.

Frozen material is often stored submerged in liquid nitrogen (LN2) Dewars. LN2 has a temperature of −196° C. and is much colder than necessary for stable storage, but has the advantages of being inexpensive and readily available. Cold storage can also be accomplished in the cold vapor space that forms above a pool of LN2, which avoids concerns about contamination by LN2. Mechanical freezers operating between −80° C. and −150° C. are yet another method of cold storage.

Vitrification is an alternative to freezing for the preservation of biological material (e.g., see U.S. Pat. Nos. 4,559,298 and 5,217,860). In vitrification, water is replaced with one or more cryoprotective chemicals in order to completely suppress the formation of ice crystals during the drop in temperature. Unlike freezing, vitrification is not harmful to even the most complicated of living systems. Vitrification creates a "glass" state. The entire cell or tissue mass becomes a glass below the glass transition temperature, permitting storage at reduced temperatures for indefinite periods without structural alteration. Storage methods for vitrified cells or small tissue samples are the same as those for freezing.

The absence of structural damage makes vitrification attractive for cryopreservation of organs and other organized tissues. However vitrification of large objects involves problems that don't exist for small (microliter) objects (Fahy, et al., "Physical problems with the vitrification of large biological systems," *Cryobiology* 27, pp. 492–510 (1990)). A major problem in vitrification is fracturing. Fracturing can occur if large objects are cooled far below the glass transition temperature, such as to liquid nitrogen temperature. Avoiding fracturing typically requires storing within 10° C. to 20° C. of the glass transition temperature. The possibility of fracturing is also reduced if an annealing process is performed in which the temperature approaches the final storage temperature sigmoidally, and very slowly (Baudot, et al., "Physical Vitrification of Rabbit Aortas without any Fracture," *Cryobiology* 43, p. 375 (2001)).

Presently available storage systems are designed to accommodate many objects, which are placed in a single isothermal or poorly-controlled vapor environment. These systems are not suitable for banking of large tissue masses where fracturing is a concern. Furthermore, annealing protocols require the storage temperature to be manipulated over potentially long periods of time. Different objects must be held at different temperatures, depending on the phase of their annealing process. Different objects may even have different final storage temperatures because the glass transition temperature can differ depending on the cryoprotectant mixture used to treat the object.

Accordingly, a need exists for devices that can store materials at cryogenic temperatures in a controlled temperature environment.

SUMMARY OF THE INVENTION

The present invention provides devices and methods for storing materials at cryogenic temperatures. The storage devices of the invention are adapted for placement into a cold source at cryogenic temperatures and for maintaining a temperature chamber in the device and materials stored therein at the cryogenic temperature. Such adaptation involves constructing the device such that it can be placed into a cold source or maintained at a cryogenic temperature while maintaining structural integrity and maintaining a seal, and is able to store biological materials at cryogenic temperatures for a period of years without structural failure, leakage, or contamination of the material in the temperature chamber. The devices of the invention enable the user to store material for long periods of time at a uniform cryogenic temperature.

The devices of the invention are useful for transporting or storing biological material at a target temperature. The temperature chamber is maintained at a uniform arbitrary temperature, which need not equal the temperature of liquid nitrogen or any other specific material. A storage device of the invention is maintained in an environment that allows a positive or zero net heat flow from the temperature chamber to the environment external to the storage device when the chamber is at the target temperature. In one embodiment electrical heat is applied to the temperature chamber or thermally conductive container as necessary to maintain the temperature chamber at the target temperature.

Thus, the present invention provides devices and methods for the cryogenic storage of biological material. In a first aspect the invention provides a device for storing material at a cryogenic temperature. The device includes a) a temperature chamber defined by a thermally-conductive container; b) at least one layer of thermal insulation surrounding the thermally-conductive container; and c) one or more heat sources thermally connected to the thermally-conductive container.

In one embodiment the device includes a control apparatus for controlling or regulating a supply of heat to the thermally-conductive container from the one or more heat sources. In various embodiments the thermally-conductive container is made of aluminum, copper, a thermally conductive ceramic, steel, or another thermally conductive material. In one embodiment the device also has at least one temperature sensor that detects the temperature in the temperature chamber. In another embodiment the device has two or more temperature sensors that detect the temperature at two or more distinct locations on or within the thermally-conductive container. The control apparatus causes heat to be supplied by the heat sources located on or within the thermally conductive container so as to maintain a set temperature for the temperature chamber. The control may be by means of passive control (user adjustment) of heater power, or active control by means of on/off control (turning heat on when the temperature drops below the set temperature), proportional-integral (PI) control, proportional-integral-derivative (PID) control, or any other algorithm suitable for the purpose of controlling heater power or duty cycle to maintain a desired set temperature. The set temperature can be adjusted using the control apparatus, or by another means such as adding or reducing thermal insulation in areas of the device. The heat sources are thermally connected to two or more distinct locations on or within the thermally conductive container and supply heat to the distinct locations to maintain a uniform temperature in the temperature chamber. The two or more heat sources can be thermally and electrically connected to the thermally conductive container.

In one embodiment the device also includes or is situated in a cold source that draws heat from the thermal insulation. Thus in one embodiment the invention provides an assembly having a device of the present invention within or in contact with a cold source. The cold source is maintained at a temperature equal to or less than the temperature in the temperature chamber, and therefore heat flows from the temperature chamber to the cold source. In various embodiments the "cold source" is a cryogenic Dewar containing liquid nitrogen or a layer of liquid nitrogen vapor. In other embodiments the cold source is a container containing a cryogenic material, one or more "cold fingers," or one or more thermoelectric piles. Cold sources can be situated within, near, against, or otherwise in thermal contact with the insulation of the device. In another embodiment the cold source is a mechanical refrigeration or freezer device that a storage device of the invention can be placed into. The cold source need not be a container that a storage container is placed into, but can also be liquid cryogen poured onto a storage container of the invention to maintain the set temperature for the temperature chamber during transport or another procedure. In various embodiments the thermal insulation is aerogel (e.g., evacuated aerogel), perlite, vermiculite, polyurethane (e.g. foam), polystyrene (e.g., foam), glass fiber, cellulose fiber, polyester fiber, polyethylene (e.g., foam), polyurethane (e.g., foam), polystyrene (e.g., foam), polyisocyanurate (e.g., foam), high vacuum insulation (superinsulation), or another thermally insulating material. In yet another embodiment a plurality of storage devices of the invention are located inside of a cold source. For example, two, three, four, five, or more, or any number up to and including 25 storage containers can be located inside a cold source. The cold source can be a liquid cryogen Dewar. Depending upon the size of the cold source, more than 25 storage devices can also be located inside the cold source. In one embodiment the cold source is located external to the insulation and heat flows from the temperature chamber to the cold source.

By "cryogenic temperature" is meant a temperature of 4° C. or lower, or 0° C.±4° C., or −20° C. or lower, or −35° C. or lower, or −50° C. or lower, or −75° C.±5° C,. or −100 ° C,. or −135° C.±5° C., or about −150° C. or lower. About means plus or minus 10%. In one embodiment the storage devices of the invention are adapted for the storage of biological material at −135° C.±5° C. By "uniform" is meant that the material is stored for a long period of time (e.g., a period of years) with a less than 20° C. fluctuation in the temperature of the temperature chamber. In other embodiments the material can be stored at a uniform cryogenic temperature for a long period of time (e.g. a period of years) with a less than 10° C. fluctuation in the temperature chamber.

By "thermally conductive" is meant that the material has the ability to transfer heat. In various embodiments the thermally conductive materials used in the invention have a thermal conductivity of at least 10 W/m-K, or at least 20 W/m-K, or at least 50 W/m-K, or at least 100 W/m-K, or at least 150 W/m K, or at least 200 W/m K, or at least 250 W/m K, or at least 300 W/m K. The thermally conductive container defines or surrounds the temperature chamber, but allowing that an area of the thermally conductive container can be interrupted to provide access to the chamber through an opening. The opening can be sealed with a door provided in the thermally conductive container, or the opening can simply be covered with thermal insulation. The thermally conductive container is adapted so that it can be wrapped in or encompassed by a layer of thermal insulation and maintain its form at cryogenic temperatures, for example when placed into a cold source such as a LN2 Dewar or another cold source.

Thermal insulation refers to material having very low thermal conductivity. Examples of thermal insulation include, but are not limited to, glass fiber, cellulose fiber, polyester fiber, polyethylene foam, polyurethane foam, polystyrene foam, polyisocyanurate foam, aerogel, perlite, vermiculite. Open cell foams and materials such as aerogel or aerogel beads (bulk density 81 kg/m$^3$), opacified aerogel beads (bulk density 94 kg/m$^3$, carbon black R300), and perlite powder (bulk density 115 kg/m$^3$, 50×50 mesh) can also be used with enhanced effectiveness with moderate vacuum. In other embodiments the thermal insulation is a high vacuum chamber with multi-layer superinsulation (bulk density 92 kg/m$^3$, e.g., 60 layers aluminum foil and fiberglass paper), such as the insulation comprising a cryogenic dewar. In another embodiment the thermal insulation is a vacuum chamber. In various embodiments the thermal insulation has a thermal conductivity (k value) of 30 mW/m-K or less at ambient pressure, 3 mW/m-K or less at 10 torr pressure, 0.1 mW/m-K or less at high vacuum.

By "high vacuum insulation" or "super insulation" is meant high vacuum dewar insulation. This type of insulation refers to insulation formed when vacuum is sufficient so that the mean free path of molecules is comparable to or greater than the dimensions of the vacuum space. In one embodiment this vacuum occurs when the pressure is 10$^{-3}$ torr or less. In one embodiment the insulation further includes layers of reflective "superinsulation" to prevent or reduce radiative heat transmission.

A "temperature chamber" refers to a sealable space or area within a thermally conductive container. The temperature chamber is defined by the thermally conductive container by being surrounded by the walls of the thermally conductive container or by thermal insulation, or a combination of the two. In one embodiment the temperature chamber is surrounded by the thermally conductive container, except that an opening is provided (such as a lid) in the thermally conductive container to provide access to the chamber, and the opening can be sealed with thermal insulation. Thus, the thermally conductive container can be interrupted at the point of access, and the temperature chamber is said to be "substantially surrounded" by the thermally conductive container. The temperature chamber can be sealable so that when it is placed into a cold source the materials inside the chamber do not become contaminated or exposed to the external environment outside the chamber when placed into a cold source at cryogenic temperatures.

The "heat sources" are any source of heat. In one embodiment the heat source is a resistor or electric heating element that heats up when electrical current is passed through the resistor, thereby generating heat. The resistors can be attached or otherwise thermally connected on or within the thermally conductive container. In another embodiment the heat source is a thermally conductive material that transmits heat through a material to the thermally conductive container.

By "thermally connected" is meant connected in such a manner as to transmit heat. When the heat source is "thermally connected directly" to the thermally conductive container, the heat source is located on or within the thermally conductive container and supplies heat directly thereto, and not solely through another material or avenue. Thus, the heat source can utilize wires that pass through the thermal insulation to a resistor located on the thermally conductive container. In one embodiment the thermally conductive container is electrically wired so that one or more resistors located on or within the thermally conductive container can be made to generate heat. Sufficient resistors are provided so that the temperature in the temperature chamber can be kept within 2° C. of any other part of the container. Thus the heat source is thermally connected to the thermally conductive container when the heat source can provide heat to a part of the container. In one embodiment the heat source provides heat directly to the thermally conductive container and does not provide heat directly to the thermal insulation (although the thermal insulation will eventually receive heat that was provided to the thermally conductive container). "Electrically connected" means connected to electric wiring that is connected to a control apparatus or other device that generates power that flows through the wires to a device (e.g., heat source) connected to the wiring.

In another embodiment of the invention the heat sources are connected to the thermal insulation of the device, whether in addition to or instead of the heat sources connected to the thermally conductive container. The heat sources can be connected either outside of the insulation or within the insulation layer. Heat thus flows from the heat source to the temperature chamber to maintain the temperature chamber at the target temperature.

In another aspect the present invention provides methods for storing biological material at a cryogenic temperature. The methods involve placing biological material to be stored at a cryogenic temperature in a device of the invention, placing the device into a cold source, and maintaining the temperature chamber at the cryogenic temperature. In one embodiment the device is placed within or in contact with a cold source that draws heat from the thermal insulation, which in turn draws heat from the temperature chamber. The cold source maintains the thermal insulation at a cryogenic temperature equal to or less than the temperature in the temperature chamber. The biological material can be any material from a biological source such as, for example, biological tissues, organs, and biological cells. In one embodiment the cryogenic temperature is −135° C.±5° C.

In another aspect the present invention provides a device for storing material at a cryogenic temperature. The device contains a temperature chamber defined by a) a thermally-conductive container; b) at least one layer of thermal insulation surrounding the thermally-conductive container; and c) a receptacle for cryogenic material. When arranged at a target temperature, no net flow of heat occurs from the temperature chamber when the temperature chamber is at the target temperature. In one embodiment a cryogenic material is located within the device. "Temperature distribution" refers to the circumstances involving the movement of heat within and around the device. Thus the temperature distribution may be a result of the total thermodynamic interactions between the device and its environment, the placement and thickness of thermal insulation, the presence and quantity of cryogen located within or around the device, and the ambient temperature outside of the device. In one embodiment heat flows into the device from outside of the device, and thus into the temperature chamber, at the same rate that heat flows from the temperature chamber to the cryogen. Thus, there is no net flow of heat from or into the temperature chamber and the temperature in the chamber is maintained at a target temperature ±20° C. "Net flow of heat" refers to the quantity of heat entering minus the quantity of heat leaving the area in question.

DETAILED DESCRIPTION OF THE INVENTION

Figure 1:
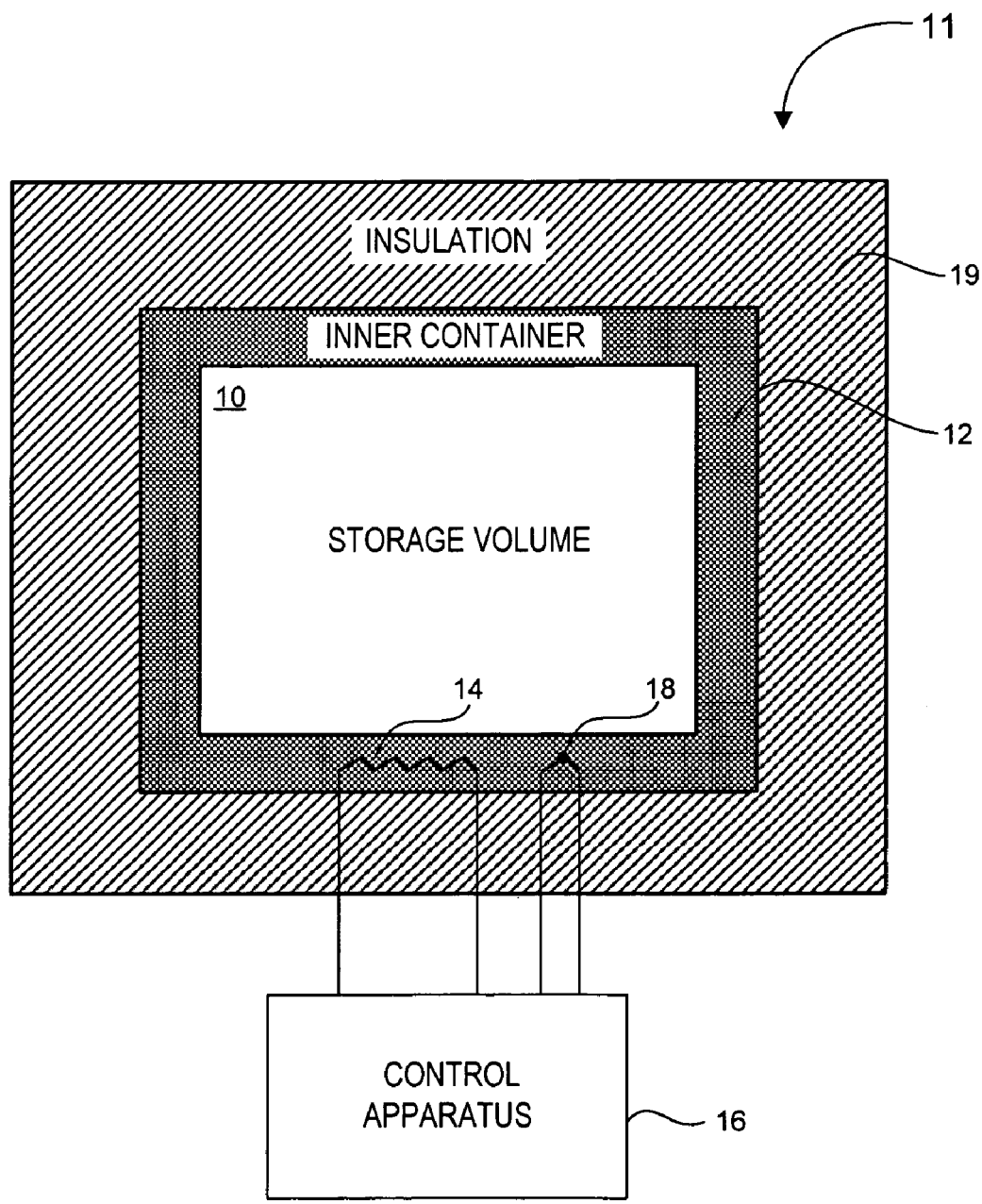
FIG. 1 shows one embodiment of the invention, which includes a temperature chamber 10, thermally-conductive container 12, and surrounding thermal insulation 19. A control apparatus 16 is depicted, which provides electric current as necessary to one or more heat sources 14 located on the thermally conductive container, and which maintain a desired temperature within the temperature chamber. The temperature is monitored by a temperature probe 18. In this embodiment the temperature control apparatus is shown external to the storage container device, but in other embodiments it is located on or inside of the device.

Referring to FIG. 1, in one embodiment of the invention a temperature chamber 10 is surrounded by a thermally conductive container 12 enclosure. The container is generally isothermal, maintaining the same temperature throughout the temperature chamber 10. The thermally conductive container 12 is made from a material that is a thermal conductor, such as the metals aluminum or copper, a thermally conductive ceramic, or another thermally conductive material or metal. The container is of sufficient thickness to maintain the desired uniformity of temperature within the temperature chamber of the device. The thermally conductive container 12 is maintained at a temperature equal to the desired temperature for the temperature chamber 10, which contains the material being held at a cryogenic temperature. Heat exchange between the temperature chamber 10 and walls of the thermally conductive container 12 causes the temperature of the chamber to become equal to the temperature of the container.

The temperature within the temperature chamber 12 can be controlled by one or more electric heat source(s) 14 (heating elements) in contact with the thermally conductive container 12. A control apparatus 16 provides electric current to the heat source(s) 14 as necessary to maintain a desired set temperature as measured by a temperature sensor 18 in contact with the thermally conductive container 12. Another embodiment places the heat source(s) 14 and/or temperature sensors 18 (e.g., thermometers) within the temperature chamber 10 inside the thermally conductive container 12, but the temperature of the thermally conductive container 12 can also be controlled directly. Under some conditions of heat flow balance, the desired set temperature can be maintained without any heater power, making the heater unnecessary in those embodiments.

Figure 16:
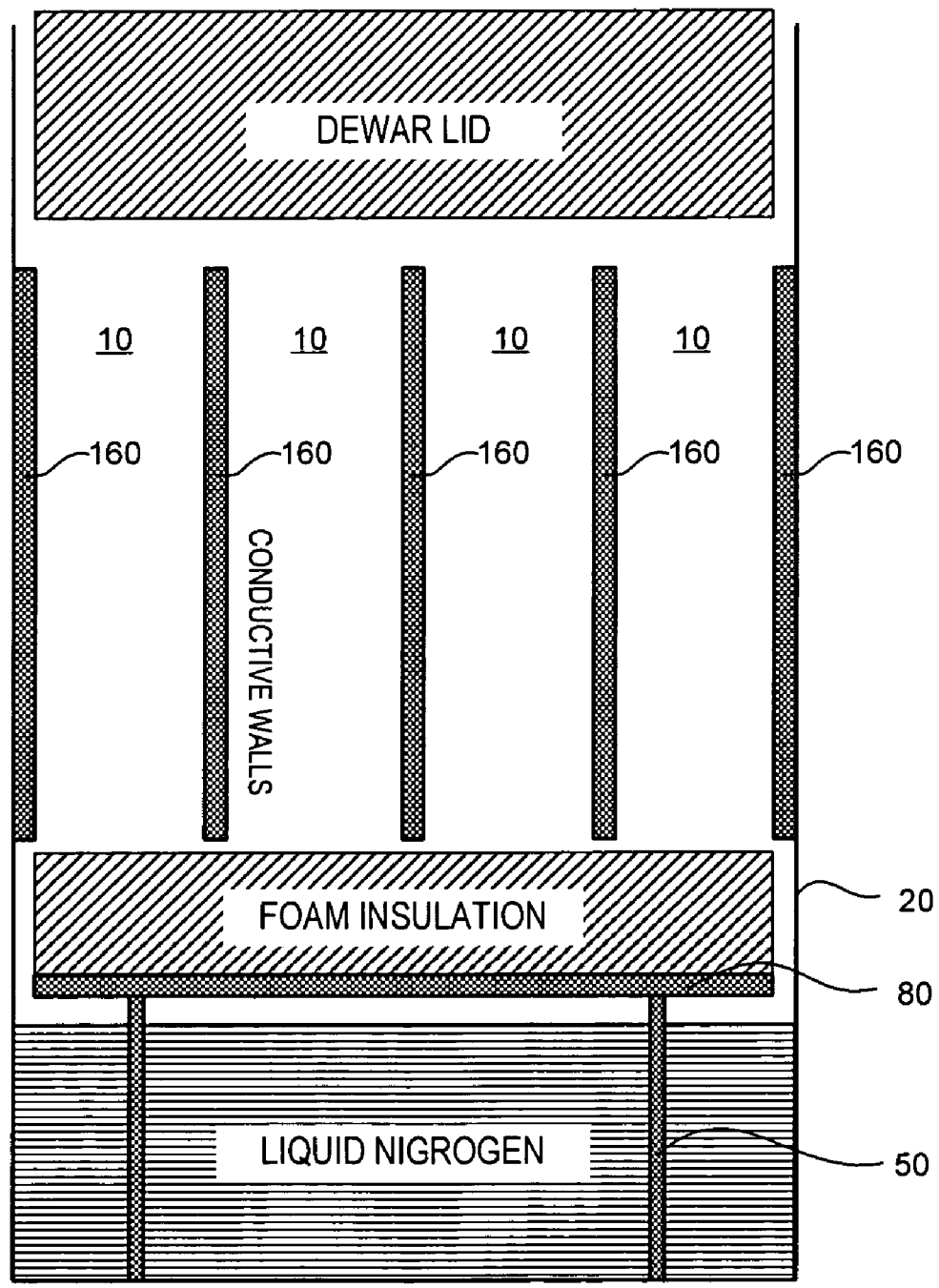
FIG. 16 illustrates a system for establishing temperature chambers of relatively uniform temperature in a Dewar 20 that requires little or no thermal conductors 50 covering the top or bottom of the storage space.

The thermally conductive container need not contain a single temperature chamber 10. In some embodiments multiple temperature chambers are arranged within a single thermally conductive container 12 to minimize temperature non-uniformity within the chambers. FIG. 16 provides an illustration of an embodiment where non-contiguous thermal conductors 50 are used across multiple temperature chambers 10. With this configuration the need for thermal conductors covering the top and bottom of the temperature chambers can be reduced or eliminated.

In a method of the invention a storage container device containing material to be stored at a cryogenic temperature is placed in contact with a cold source that is colder than the thermally conductive container. This results in a net flow of heat from the temperature chamber and thermally conductive container to the cold source. Heat is supplied by one or more heat sources to areas on or within the thermally conductive container, as necessary to maintain the set temperature for the temperature chamber in the presence of this heat flow. The insulation surrounding the thermally conductive container minimizes the flow of heat, and minimizes the occurrence of local deviations from the set temperature within the temperature chamber.

Figure 2:
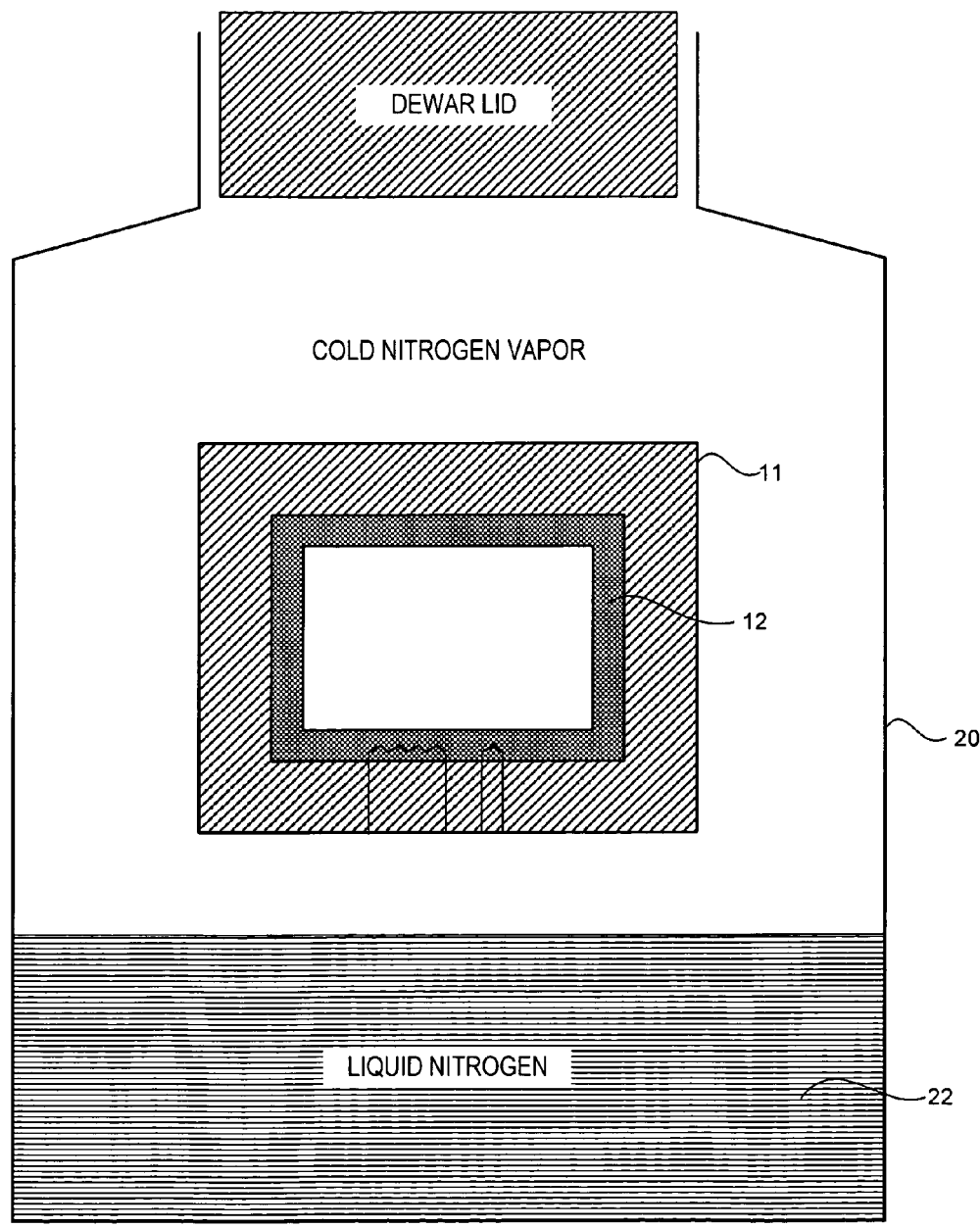
FIG. 2 shows an embodiment of the invention where the device is located inside a cold source, here a cryogenic Dewar 20 partly filled with liquid nitrogen 22.

With reference to FIG. 2, the storage container 11 can be placed inside a cryogenic Dewar 20 as a cold source. The low temperature within the Dewar can be maintained by liquid nitrogen 22 (LN2) or another cryogen. A "cryogen" or "cryogenic material" is a material that will create extremely cold conditions. Some cryogens are gases that have been cooled until they are in liquid or solid form. Commonly used cryogens include liquid nitrogen (LN2), liquid helium, liquid hydrogen, and dry ice (solidified carbon dioxide). The container can be immersed in the LN2 22 wholly or partially, or held in the vapor space above the LN2 22. The only requirement is that the environment surrounding the container have a temperature distribution such that the net heat flow out of the container is positive or zero when the thermally conductive container 12 is at the desired set temperature.

Figure 3:
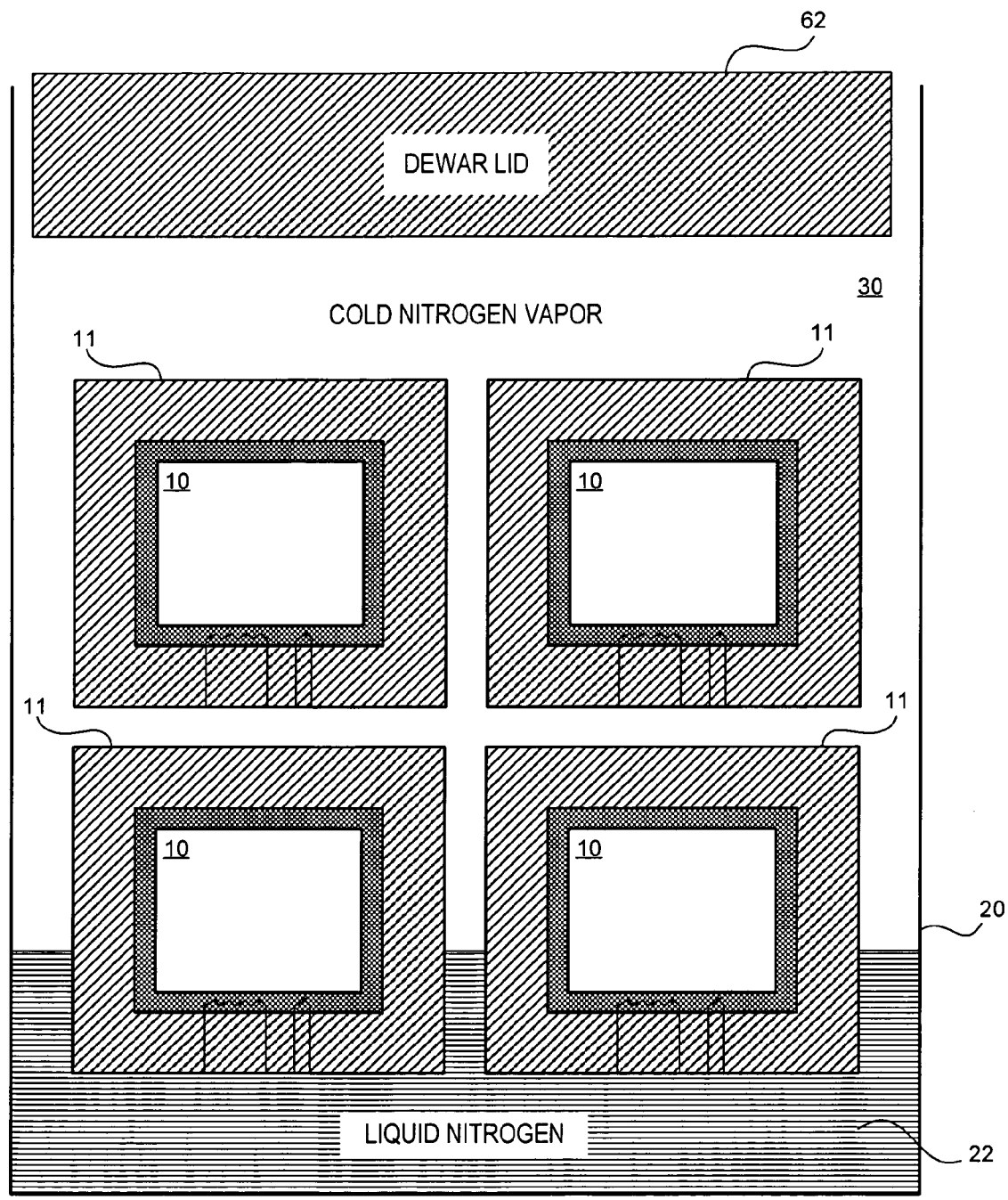
FIG. 3 shows another embodiment with multiple devices 11 within a single cryogenic Dewar 20.

FIG. 3 shows a plurality of storage containers 11 being maintained within the same cold source environment 30. In some embodiments the temperature chamber 10 of each container is maintained at a separate target temperature. The temperature surrounding each storage container 11 and target temperature of the temperature chamber 10 is such that the heat flow out of each storage container 11 is positive or zero. The insulation surrounding the individual containers also permits removal of containers from the cold source environment 30, and brief transit through air outside of the cold source, while minimizing any temperature increase in the temperature chamber. During prolonged transport procedures, LN2 or other cryogens can be poured over the container exterior while the heat source(s) maintain the desired temperature for the temperature chamber 10.

Figure 4:
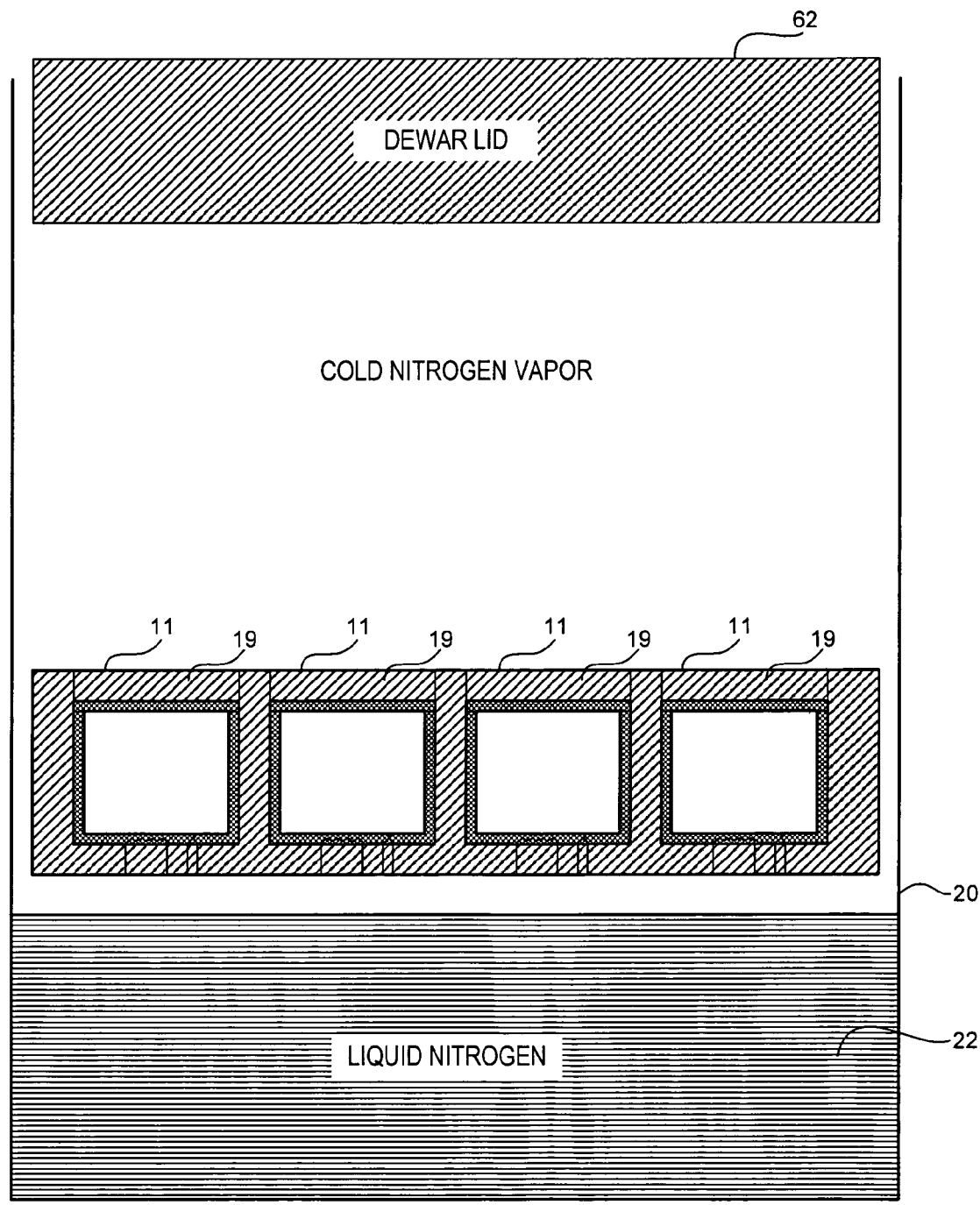
FIG. 4 shows a Dewar 20 holding multiple devices 11 and maintaining distinct temperatures for each device.

FIG. 4 shows a plurality of storage containers 11 in which the thermal insulation 19 surrounding the isothermal boundary of each container is shared. This embodiment permits many storage containers 11 to be removed and replaced as a unit, and containers can be maintained at different temperatures, as desired.

Figure 5:
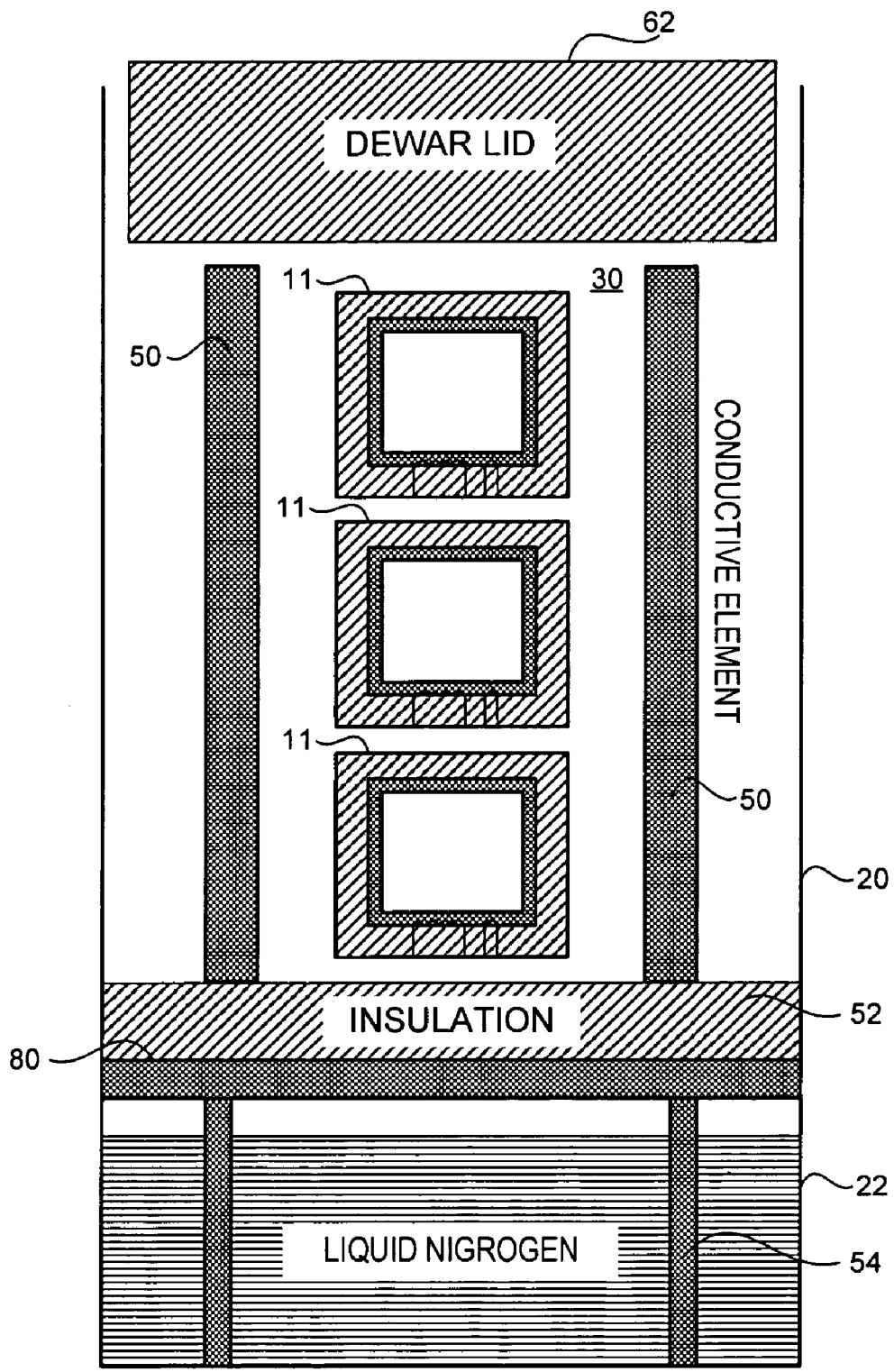
FIG. 5 shows another embodiment with multiple storage containers in the vapor space of a Dewar 20. In this embodiment the temperature of the vapor space is made more uniform by vertical thermal conductive elements 50.

FIG. 5 shows a plurality of storage containers 11 maintained within a cold source environment 30 in which the temperature is made more uniform through the use of one or more thermal conductive elements 50 that are located within the cold source. In this embodiment the conductive elements 50 cause the top region of the Dewar 20 to be colder than it would be otherwise, thus permitting containers with low target temperatures to be placed higher in the Dewar 20. The conductive elements 50 also cause the bottom region of the Dewar 20 to be warmer than otherwise, reducing the heating requirements within the lower containers. A lower layer of thermal insulation 52 is also provided above the pool of liquid nitrogen to increase uniformity of temperature throughout the Dewar. Many possible materials, shapes, and arrangements of thermal conductors 50 can achieve these objectives, including vertical sheets, bars or rods made of aluminum, copper or other thermal conductors 50. These conducting elements 50 can be in contact with container exteriors, suspended in vapor, or in contact with the Dewar inner walls. The conductive elements can be in contact with the cold source exterior wall and arranged surrounding the storage devices, whether vertically positioned or horizontally. The Dewar itself may be built with thicker interior walls to improve vapor temperature uniformity. An advantage of bars or rods is that they can be conveniently removed, inserted, raised, or lowered as necessary to achieve a desired temperature distribution around the storage containers 11. A temperature distribution that minimizes interior/exterior temperature differences of the containers will minimize the heat source power necessary to maintain the target temperature, and thus maximize the operating efficiency of the system. FIG. 5 also shows the storage devices are maintained in an environment of cold vapor that surrounds all sides of each storage container 11.

Figure 6:
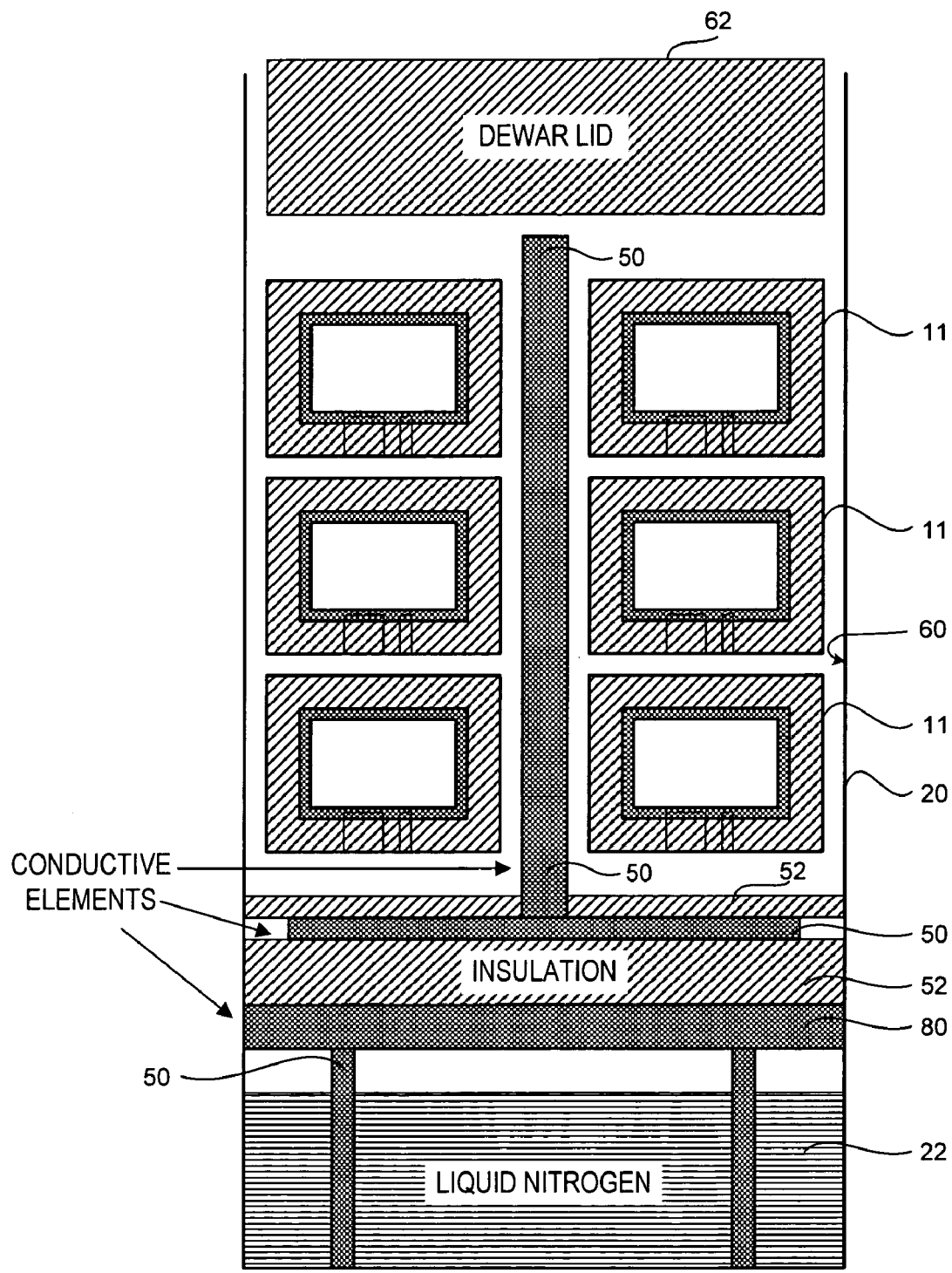
FIG. 6 shows another embodiment maintaining multiple devices 11 in a Dewar 20 by allowing only a limited area of each container to contact the cold conductive elements 50.

Yet another embodiment is depicted in FIG. 6, where most of the surface area of each storage container 11 thermally contacts other containers or the lining of the inside Dewar wall 60 (which is a poor thermal conductor). A comparatively small area of each container contacts the cold centrally located thermal conductor 50. The volume away from the cold centrally located thermal conductor 50 warms to the mean internal temperature of nearby storage containers 11, thereby minimizing container heat flows. The lining of the inside wall of the Dewar 60 (or other cold source) is a poor conductor. Suitable materials for the lining of the Dewar or other cold source include plastics and exposed foam insulation. Still other embodiments of the invention are possible. For example, thermal conductors 50 (e.g., vertically arranged) can be located in spaces between storage containers 11. These thermal conductors 50 can also be horizontally arranged, or arranged in a combination of a vertical and horizontal pattern. Still other embodiments utilize a limited thermal coupling of each container to the cold thermal conductors 50. FIG. 6 also shows that the thickness of one or more bottom layers of thermal insulation 52 between the cold thermal conductors 50 in contact with the storage containers 11 and the cold thermal conductors 50 in contact with the LN2 22 can be used to control the temperature of the cold thermal conductors 50 in contact with the storage containers 11. One or more thermal conductors 50 can be located within layers of insulation. The Dewar lid insulation 62 and heat source power applied to storage containers 11 can also be used to control this temperature.

Figure 7:
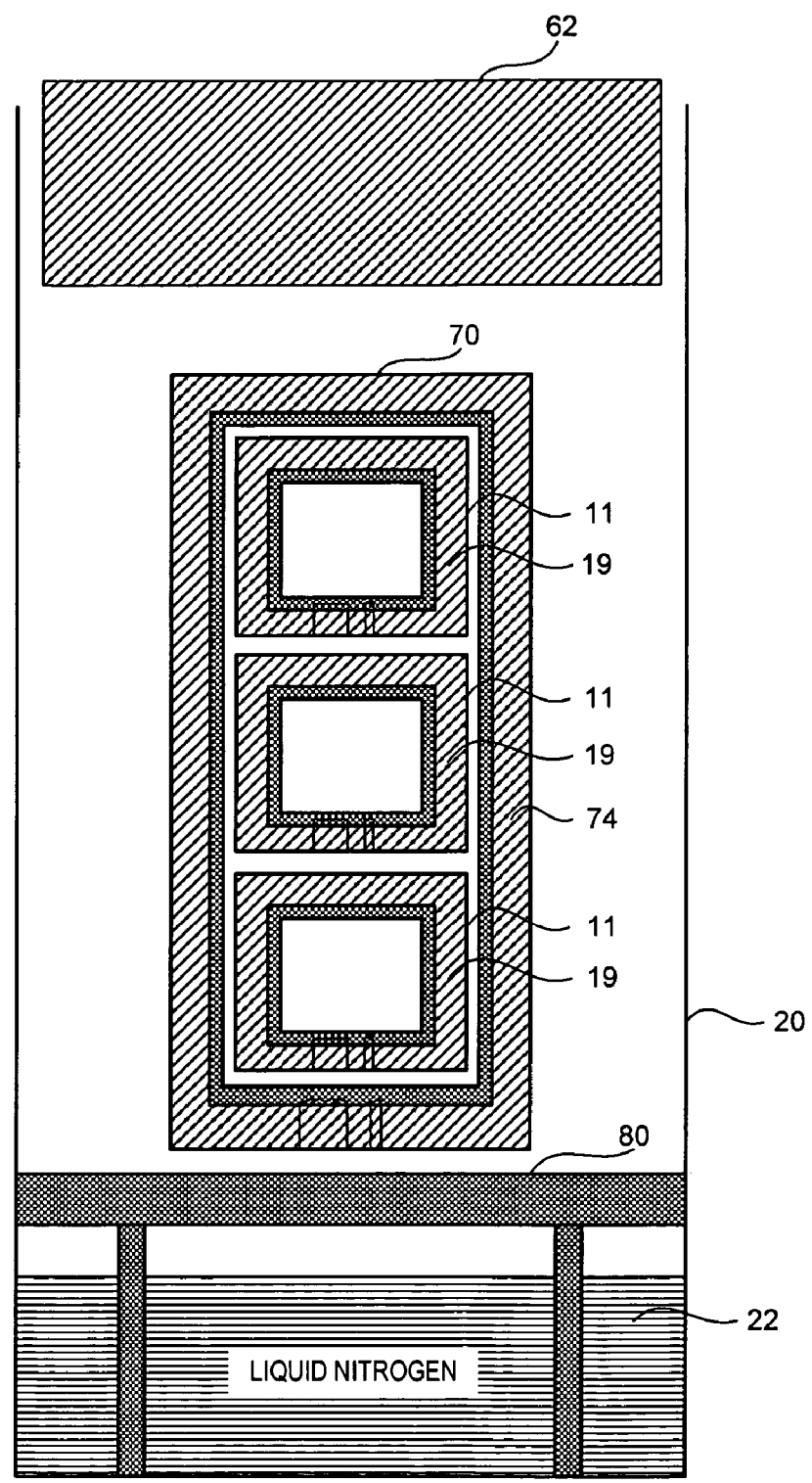
FIG. 7 shows an embodiment having three storage devices 11 nested inside the uniform temperature environment of a larger device held within a Dewar 20. A platform 80 that is a thermally conductive element holds the larger container above the liquid nitrogen is explicitly shown.

FIG. 7 depicts an embodiment where the storage containers 11 of the invention are situated in a nested configuration, meaning that smaller storage containers 11 are placed into a larger storage container 70 for storage at a cryogenic temperature. As with the smaller containers, the temperature of the larger storage container 70 can also be monitored and controlled to maximize operating efficiency of the total system. The larger storage container 70 has its own thermally conductive container 72 and layer of thermal insulation 74.

Thermally conductive elements 50 (e.g., as depicted in FIGS. 5-8) can be immersed in liquid cryogen and are useful for improving the temperature stability of systems that are dependent on cryogen levels. The platform 80 at the bottom of the Dewar (or other cold source) is also a conductive element and lifts the storage container out of the liquid cryogen and into the vapor space. The platform 80 remains at a temperature near the boiling temperature of LN2 regardless of the LN2 level. This improves the temperature stability of the vapor space above the LN2 between refills of LN2. Even in the absence of such conductive elements, a great advantage of the present invention is that the interior of storage containers is protected from temperature fluctuations in the vapor space that can accompany cryogen refills. Vertical stands 54 serve to provide a stable support for the platform and are also conductive elements.

Figure 8:
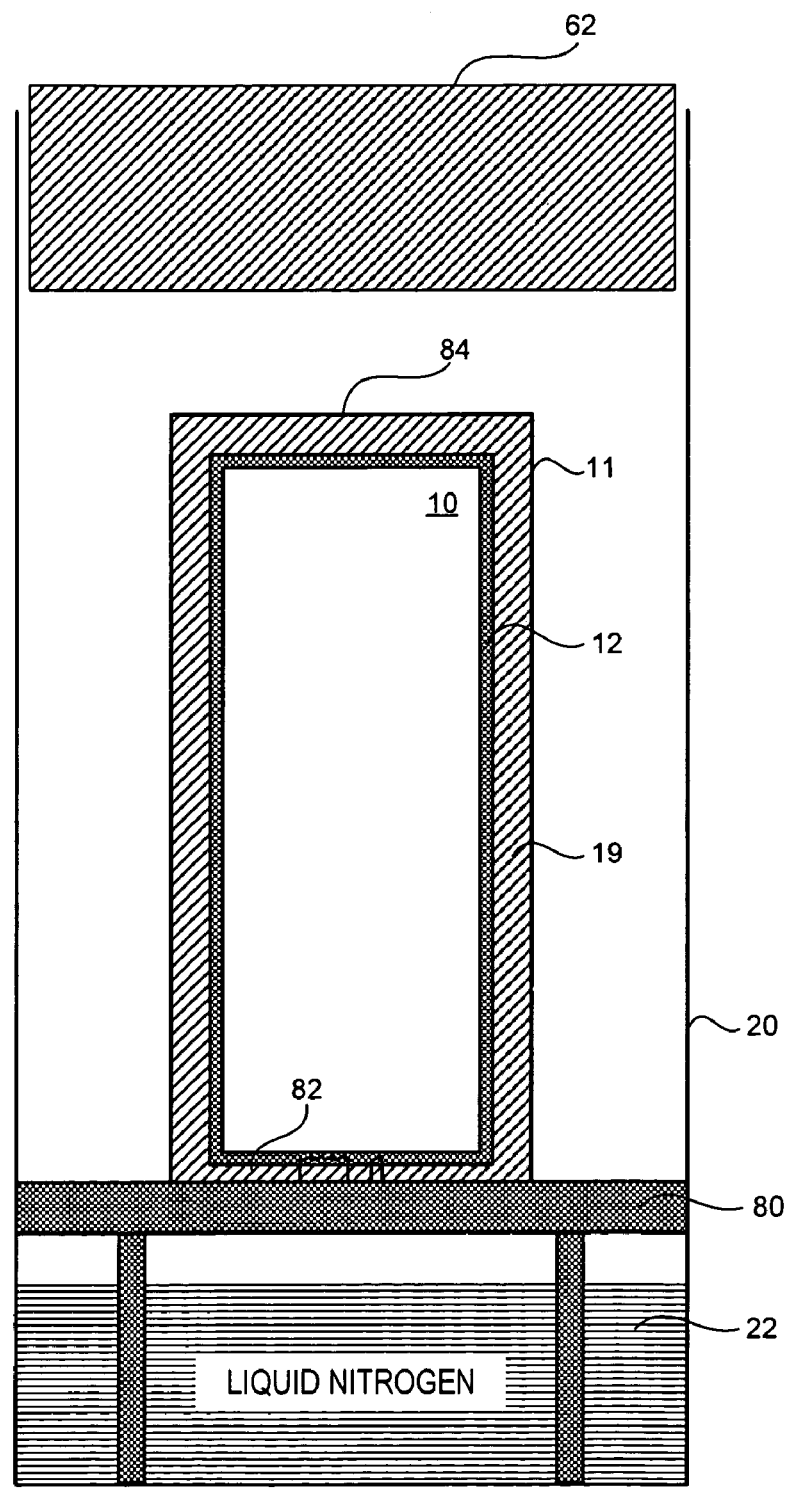
FIG. 8 shows an embodiment where the temperature chamber 10 is maintained at a temperature closer to the exterior temperature at the bottom of the container by utilizing thinner insulation 82 at that location.

FIG. 8 illustrates the principle that the environment surrounding the storage container 11 of the present invention can be of very non-uniform temperature. In the figure, the platform 80 in contact with the bottom of the container is at the boiling temperature of LN2 22, while the vapor in contact with the Dewar lid 62 is close to the ambient temperature outside the Dewar. Large environmental temperature non-uniformity is permissible provided that the thermally conductive container 12 and surrounding thermal insulation 19 are of sufficient thickness to satisfy temperature uniformity requirements within the container. The container also need not operate at a target temperature near the mean temperature of the environment. In the example shown in the figure, the insulation at the bottom of the container 82 is thinner than insulation at the top 84, thereby permitting the interior of the container to be maintained at a temperature that is closer to the temperature at the bottom of the Dewar than at the top. Other designs for fine tuning the insulation balance between the container top and bottom are also possible. For example, conductive braids penetrating the bottom insulation could be raised or lowered into the LN2 to adjust the equilibrium temperature of the container interior.

In the embodiments discussed above, a cryogenic Dewar holding a boiling cryogen is used as a cold source for the invention. But many other environments and configurations can serve as cold sources for the invention. These include, but are not limited to, vessels insulated with perlite, aerogel or foam at either ambient or soft-vacuum pressure. Cold can be maintained within the vessels by either cryogens, cold fingers, thermoelectric piles, or by placing the vessels in a mechanical refrigerator or freezer. The storage containers of the invention can be surrounded by cold vapor, cold liquids, or cold solids, or any combination thereof sufficient to generate positive or zero heat flow from the container interior. Surrounding vapor or fluids can be either static or moving.

Figure 9:
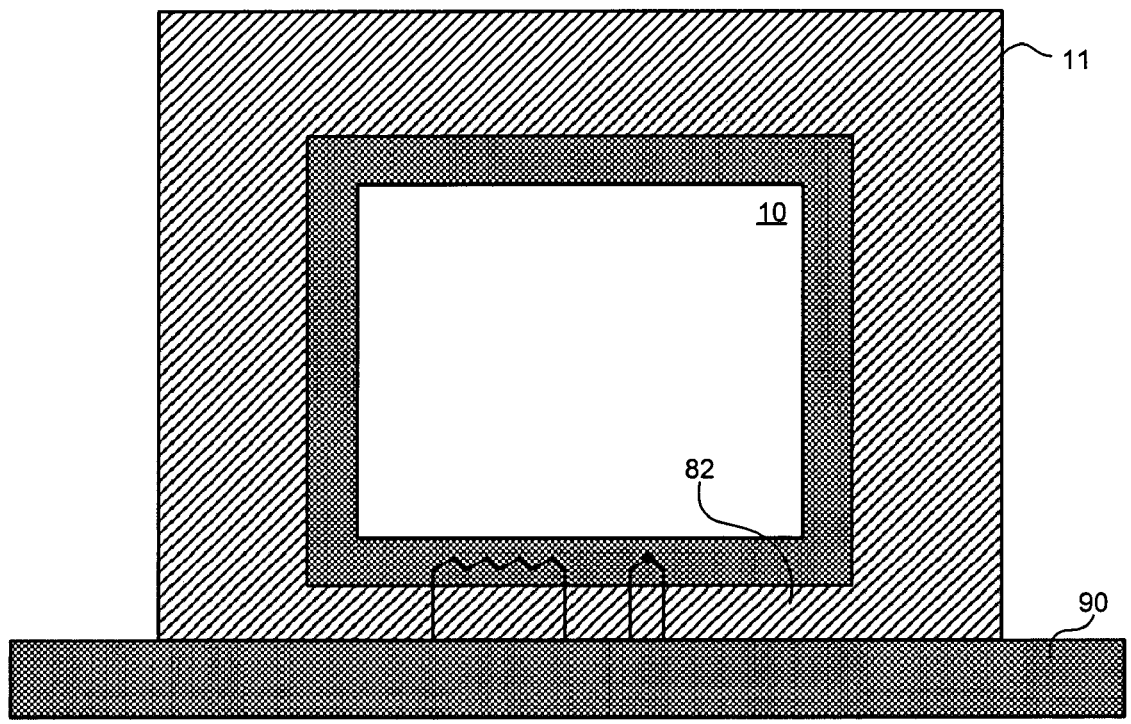
FIG. 9 shows an embodiment of the invention where a storage container device 11 is maintained outside of a Dewar by resting the device on a cold plate 90 that acts as a cold source through thin bottom insulation 82.

FIG. 9 illustrates that a vessel holding the storage container(s) 11 and cold source is not essential for the invention to work. In the figure a storage container 11 merely rests against a cold plate 90. Provided that the magnitude of the heat flow to the cold plate 90 equals or exceeds the flow of heat from the warmer temperature chamber 10, the target temperature of the temperature chamber 10 can be maintained. Continuous or intermittent pouring of cold cryogen over a container exterior is another example of a cold source or heat sink that does not require a surrounding vessel. For example, liquid nitrogen might be intermittently poured over a container during transport operations through air outside of the cold source.

While many applications of the invention involve cryogenic temperatures, the invention can also operate in other temperature ranges. For example, transplantable tissues and organs that are not cryopreserved are typically transported in ice water at 0° C. If temperatures higher than 0° C. were optimal for short-term preservation of material, the invention could be used to transport material at a stable higher temperature using melting water ice as the cold source or heat sink.

The present invention offers the advantage of a storage container that can be placed into virtually any environment where the surrounding temperature (or sufficient portion thereof) is below the target temperature for the temperature chamber, and the desired target temperature can still be maintained within the container interior. For example, if the storage containers are being maintained in a larger storage container, and the large container fails, the storage containers can be moved into any other sufficiently cold environment and will function normally. If storage containers must be moved long distances, they can be easily moved inside of simple cryogen-bearing transport Dewars or boxes. As long as power is available for the control electronics (e.g., by use of batteries), the container interiors can be maintained at a constant and uniform temperature even if the surrounding environment has a very non-uniform and poorly-controlled temperature.

Another advantage of the present invention is that it provides a "fail safe" storage system. Temperature control is purely electronic, with no moving parts that wear out. Power requirements are modest, and approach zero if the cold source environment is adjusted to minimize net heat flow from container interiors. Perhaps the most likely failure mode is failure of the cold source environment, such as a Dewar vacuum failure. In other storage systems, the sudden increase in LN2 boiling following a vacuum failure could cause either temperature rise (for materials stored submerged under LN2) or sudden temperature drop (for materials stored in vapor above LN2). But under such circumstances the present invention automatically adjusts the heat sources associated with the storage containers to maintain the target temperature of each storage container for as long as the Dewar remains sufficiently cold. This provides critical time during a failure to move the containers to another cold source environment.

Other possible system failures include electric power failure and failure of electronic control apparatus. Electric power failure causes the system to "fail cold," i.e., the storage environment slowly cools to a temperature determined by the cold source environment external to the storage container. The magnitude of this drop in temperature is easily limited by designing the system so that the external cold source environment is not far below the target temperature for the temperature chamber. Such a design also minimizes heat source power requirements. Electronic control apparatus failure causes either a "fail cold" condition described above, or a "fail warm" condition in which full power is delivered to the heater. The magnitude of either of these potential failures can be minimized by "trimming" the heat source control apparatus circuit so that power available to the heat source is limited. This is done by determining a stable operating condition for the system. A minimum heat source power level is continuously delivered to the system independent of the control apparatus, and the power available to the control apparatus could be limited. The effect of the control apparatus would therefore be confined to a narrow temperature range. In another embodiment, dual redundant controllers could also be employed.

The thermal insulation surrounding the thermally conductive container can be of many different types. The most efficient thermal insulation is high vacuum insulation, such as used within the walls of cryogenic Dewars. A Dewar containing a thermally conductive container, thermal sensor, and heating element that is placed inside another Dewar (or other cold source environment) is an example of the invention that uses such insulation. But foam or soft vacuum thermal insulation provides greater economy and design flexibility. Aerogel insulation is a particularly good thermal insulation because in its evacuated form it provides insulating values almost ten times greater than conventional foams. It therefore permits low heat leak (leading to high operating efficiency) and good temperature uniformity, while minimizing the physical size of a storage container.

The invention can combine insulation of different types. For example, in FIG. 15 the thermally conductive container 12 of the storage device 11 is surrounded by foam thermal insulation (the insulated Dewar lid 62 above, and a lower layer of thermal insulation 52 below), and the high vacuum insulation of the Dewar walls on the sides (not shown). The liquid nitrogen 22 below the lower thermal insulation 52 is a cold source. The walls of the thermally conductive container 12 and temperature chamber 10 within will attain a temperature dependent on the relative thickness of the lower layer of thermal insulation 52 and Dewar lid insulation 62, as well as the proximity of the liquid nitrogen 22 and the use of thermally conductive elements 50. If these thicknesses and proximities are chosen correctly, a desired or set target temperature in the temperature chamber 10 can be achieved and maintained without the use of a heat source other than the environment outside of the device. In these embodiments a temperature distribution is arranged such that there is no net heat flow from the temperature chamber when the temperature chamber is at a set target temperature. Such a distribution can be arranged by utilizing varying thicknesses of insulation in the device, such that the temperature chamber is maintained at a temperature between the LN2 and the temperature outside of the device. The temperature chamber 10 will therefore be maintained within a uniform temperature range and can be used for direct storage of items, or as a temperature-optimized cold source environment for smaller individual storage containers of the present invention. A platform 80 can hold the lower level of insulation and thermally conductive elements 50 are also included. If multiple vertical thermal conductors 160 are distributed across the cross section of the storage space, as depicted in FIG. 16, the need for thermal conductors covering the top and bottom of the temperature chamber can be reduced or eliminated.

The invention is further described in specific embodiments with reference to the following non-limiting examples.

EXAMPLE 1

Manufacture of a Storage Container Device

A cylindrical aluminum container of 30 cm diameter, 30 cm height, and 3 mm thickness is obtained. The thermally conductive aluminum container has a temperature chamber within and is surrounded on all sides by a foam insulation of 5 cm thickness. The insulation has a thermal conductivity of 0.03 W/mK. The top portion of the container is formed as a lid to allow access to the temperature chamber inside. The container is placed inside a Dewar (as shown in FIG. 2) such that the bottom of the container rests on or near the surface of LN2 inside the Dewar. The bottom of the container is at a temperature of approximately −196° C. The temperature of the vapor in the Dewar is stratified such that the top of the container is at a temperature of −120° C. The target temperature for the temperature chamber is −150° C.

Figure 11:
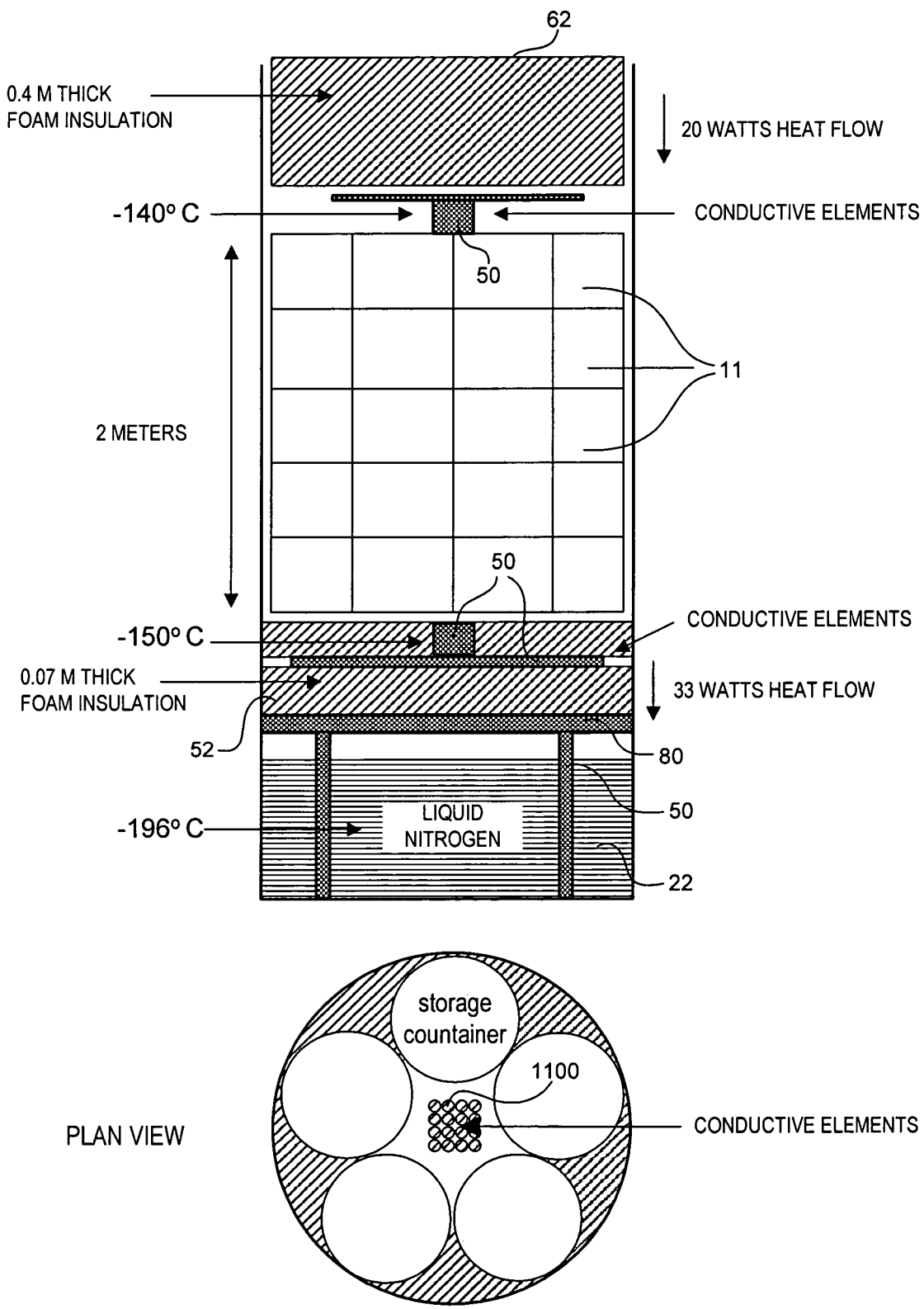
FIG. 11a shows an embodiment where 25 separate containers are maintained at an internal temperature near −135° C. in a large cryogenic Dewar 20. Shown are the storage containers 11, Dewar lid 62, liquid nitrogen 22, and thermally conductive elements 50.
FIG. 11b shows a plan view of the same device.
Figure 12:
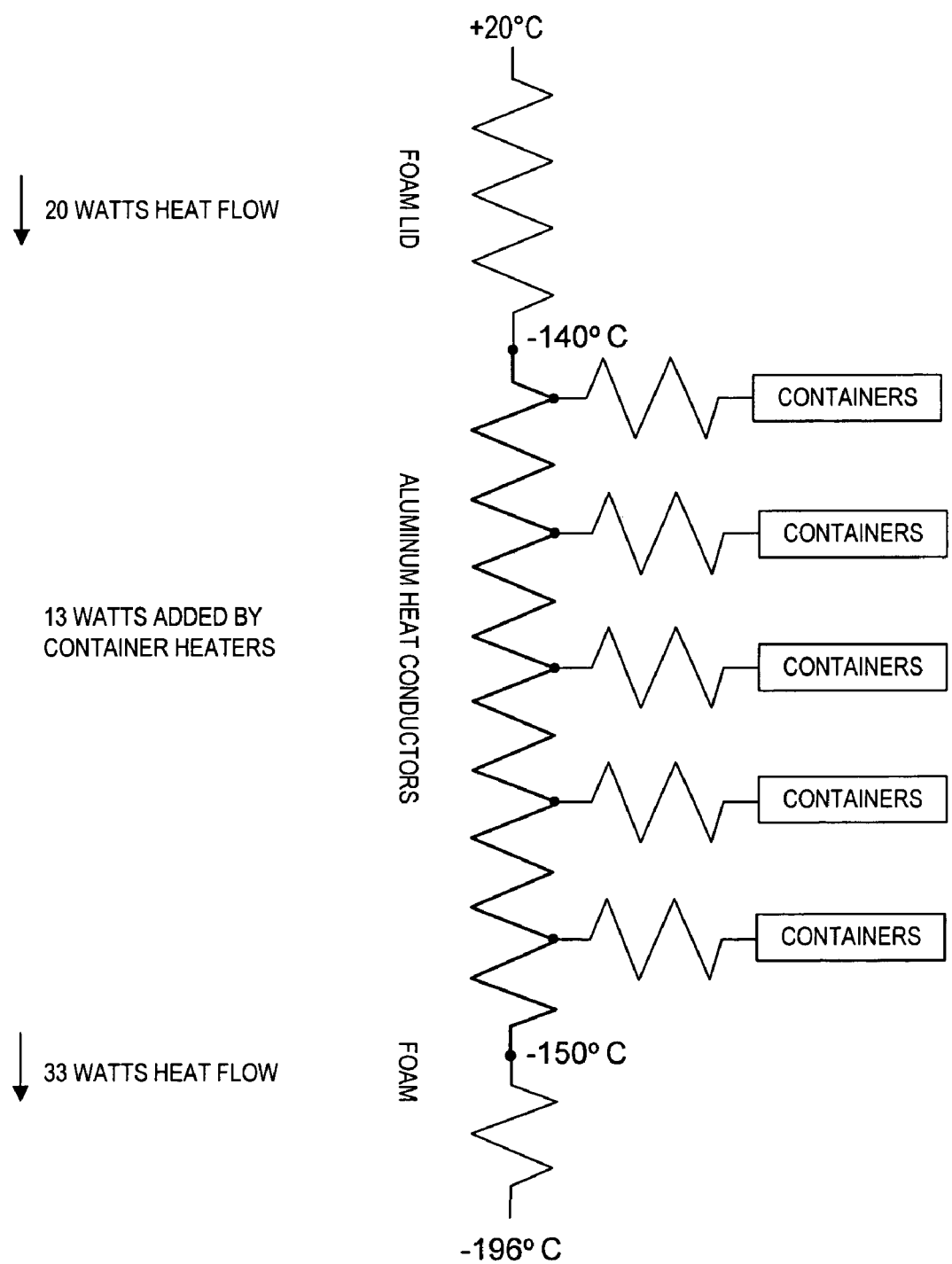
FIG. 12 is a schematic illustration of the thermal couplings and heat flows of the system of FIG. 11. Thermal couplings between adjacent storage containers are not shown.

In another embodiment a Dewar similar to that shown in FIG. 11 is obtained having a diameter of 1 meter and an inner wall of 1 mm thick stainless steel (thermal conductivity k=12 W/mK). Aluminum rods or bars 1100 2 m tall and of cross sectional area 0.02 m² stand in the middle of the Dewar between the Dewar lid 62 and insulated floor having the lower layer of insulation 52 above the liquid nitrogen, similar to that depicted in FIG. 11. With the dimensions described, the temperature at the top of the aluminum cold elements is −140° C., and is −150° C. at the bottom. The heat flows are as shown in FIGS. 11 and 12. The insulating foam disks and surrounding steel walls contribute approximately equally to the heat flows. The thermal couplings from which the heat flows are calculated are shown schematically in FIG. 12.

EXAMPLE 2

Thermal Flow

The external surface area of the container of Example 1 is about 0.75 square meters. If the bottom half of this surface area is at −196° C., and the temperature chamber in the interior is at −150° C., the heat flow out of the container will be 11 watts, and the LN2 consumption will be about 5 liters per day or less. Similarly, if the top half of the container is at −120° C., the heat flow into this half will be approximately 7 watts. The difference between the 7 watt inflow and 11 watt outflow is made up by 5 watts of electric heat applied to the bottom of the thermally conductive container.

Figure 10:
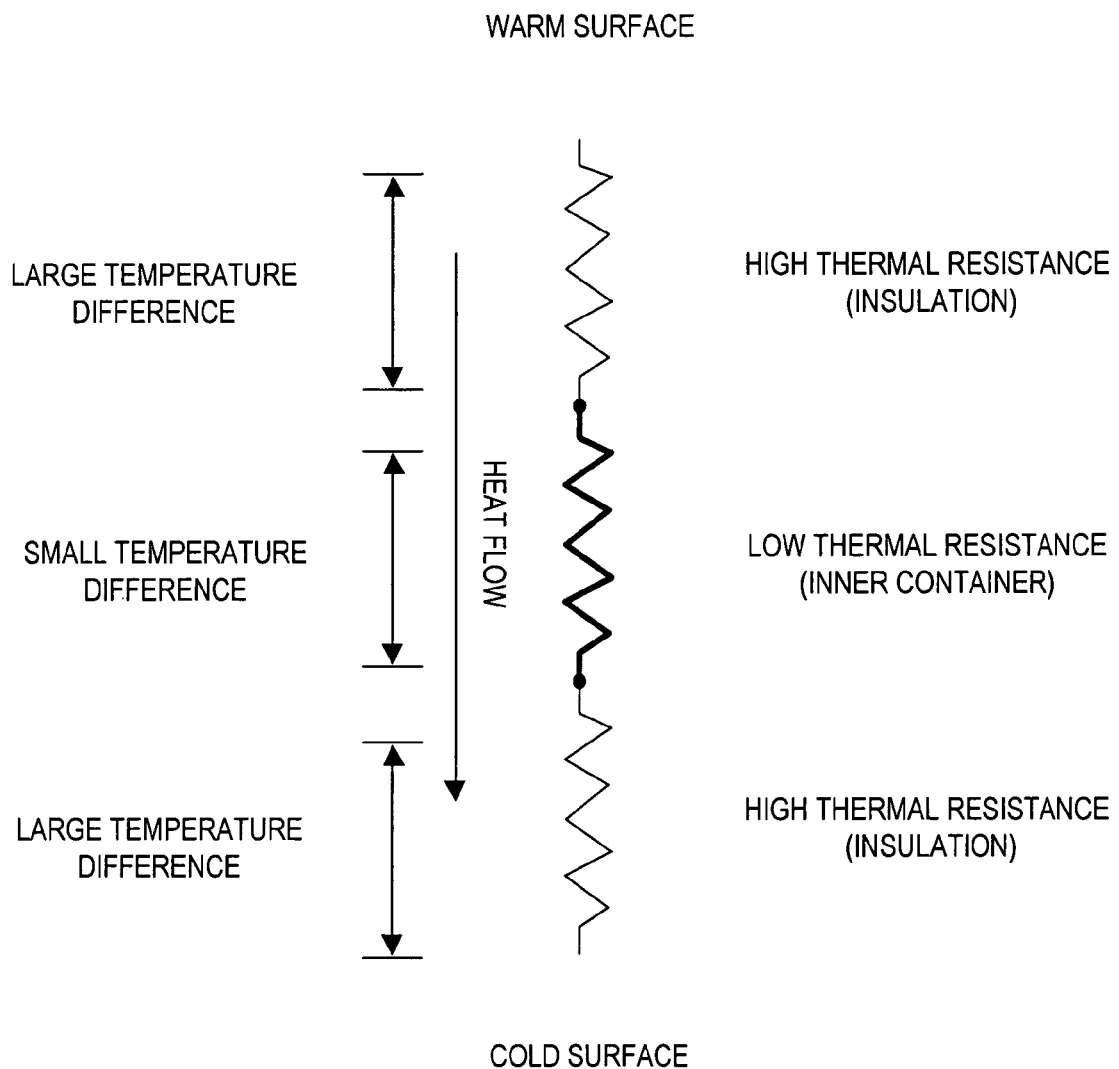
FIG. 10 illustrates the concept of different thermal resistances on heat flow that occurs when the invention is held in an environment of non-uniform temperature.

Seven watts travels from the top to the bottom of the aluminum thermally conductive container. The wall of the thermally conductive container has a cross sectional area of 0.003 square meters, and aluminum has a thermal conductivity of approximately 240 W/mK. The top-to-bottom temperature difference of the thermally conductive container is therefore only 3° C. despite the nearly 80° C. external temperature difference. This is verified by the formula:

$$\frac{3° \text{C.} \times 0.003 \text{ m}^2 \times 240 \text{ W/mK}}{0.3 \text{ m}} = 7 \text{ watts,}$$

which is an application the standard Newton formula for heat flow:

$$\frac{\text{Temperature Difference} \times \text{Surface Area} \times \text{Thermal Conductivity}}{\text{Thickness}} = \text{Heat Flow,}$$

which is used to compute heat flow in these examples. The mechanism by which a large external temperature difference is converted to a small internal difference is conceptually illustrated in FIG. 10.

If evacuated aerogel insulation is used in the example instead of foam, the heat flows are reduced by a factor of ten. The LN2 consumption will be 0.5 liters per day, electric power consumption 0.5 watts, and the internal temperature difference 0.3° C.

In another embodiment a device as depicted in FIG. 11 and described in Example 1 is obtained. The storage space within the Dewar is filled with a total of 25 foam-insulated storage containers of the type described in Example 1. Resistive heating is applied to the interior of each storage container to maintain a target temperature of −135° C. Therefore the mean temperature difference between container interiors and the central cold element in the Dewar is 10° C. An individual storage container surrounded on all sides by a temperature ten degrees colder than the container interior leaks 5 watts of heat. However as shown in FIG. 11, only a small part of each container contacts the central cold elements. If the amount of thermal contact is adjusted so that effectively 10% of each containers' surface area contacts the central cold zone, then heat will flow from the containers to the central cold elements at a rate of 0.5 watts per container, or 12.5 watts total. This heat is in addition to the 20 watts leaked into the top of the Dewar, for a total of 33 watts flowing into the liquid nitrogen. This translates into a LN2 consumption rate of 17 liters per day for holding 25 storage containers.

While the calculations above are based on the container interior maintained at −135° C., considerable margin available for individual adjustment of container temperature. There is no upper limit on the container temperature, provided that a container temperature is not so high that it leaks more heat than the cold elements can remove, thereby leaking heat to neighboring containers. The lower limit of container temperature approaches the temperature of the cold source it is placed in, again provided that neighboring containers do not leak more heat than the cold element can remove.

EXAMPLE 3

Heat Sources and Heat Distribution

Figure 13:
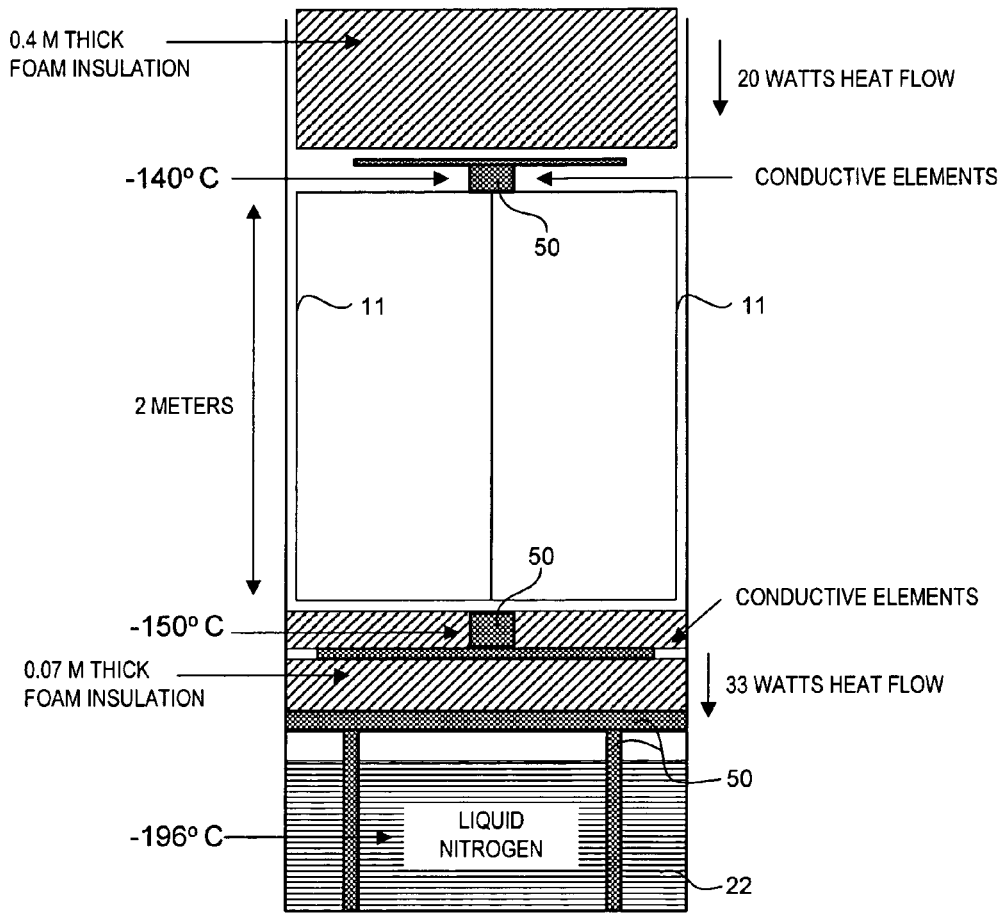
FIG. 13 illustrates an embodiment where three large storage container devices 11 are maintained at an internal temperature near −135° C. in a cryogenic Dewar. Shown are the liquid nitrogen 22 and thermally conductive elements 50.
Figure 13:
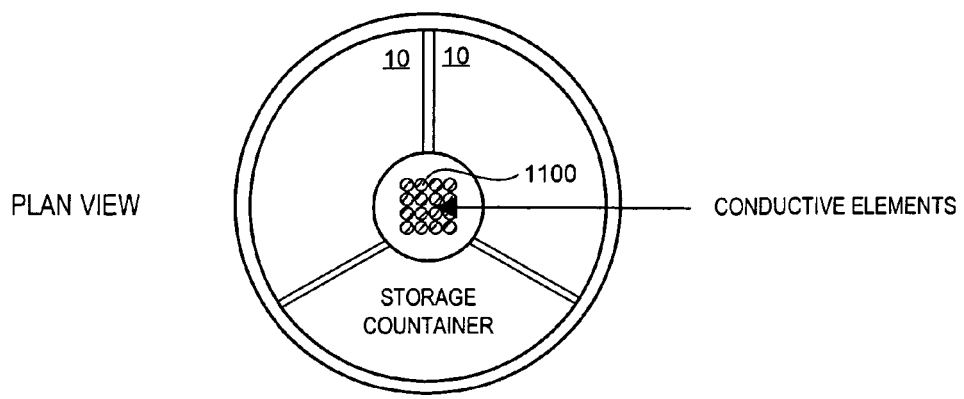

FIG. 13 depicts an example that is analogous to the setup described in Example 1, except that three large storage containers are placed in the Dewar instead of 25 smaller ones. Each storage container device is 2 meters long and has a temperature chamber defined by a 3 mm thick aluminum thermally conductive container. The containers have about 5 cm thick conventional foam insulation on all sides. The internal temperature is 135° C., and thermal contact with the central cold elements 1100 is arranged so that there is a 4 watt heat flow out of each storage container. System performance is 17 liters per day LN2 consumption.

In some embodiments multiple internal temperature sensing and heating points are used. In one embodiment a single resistive heater encircles the inner diameter of a container and supplies the requisite heating with only a 3° C. temperature variation within the container. In one embodiment independently controlled heaters at the top, middle, and bottom of the container interior reduce temperature non-uniformity to less than one degree.

In another embodiment multiple sensors/heaters are used to reduce temperature non-uniformity along any thermally conductive container walls that are emitting heat to the external environment. In cases where the thermally conductive container wall is absorbing heat from the external environment, extra heaters do not improve temperature uniformity in these regions. The thermal conductivity and thickness of walls that absorb heat from the external environment must be great enough to transport the heat to wall regions where the heat can leave the container without causing unacceptable temperature gradients along the way.

EXAMPLE 4

Aerogel-Insulated Storage Containers

Figure 14:
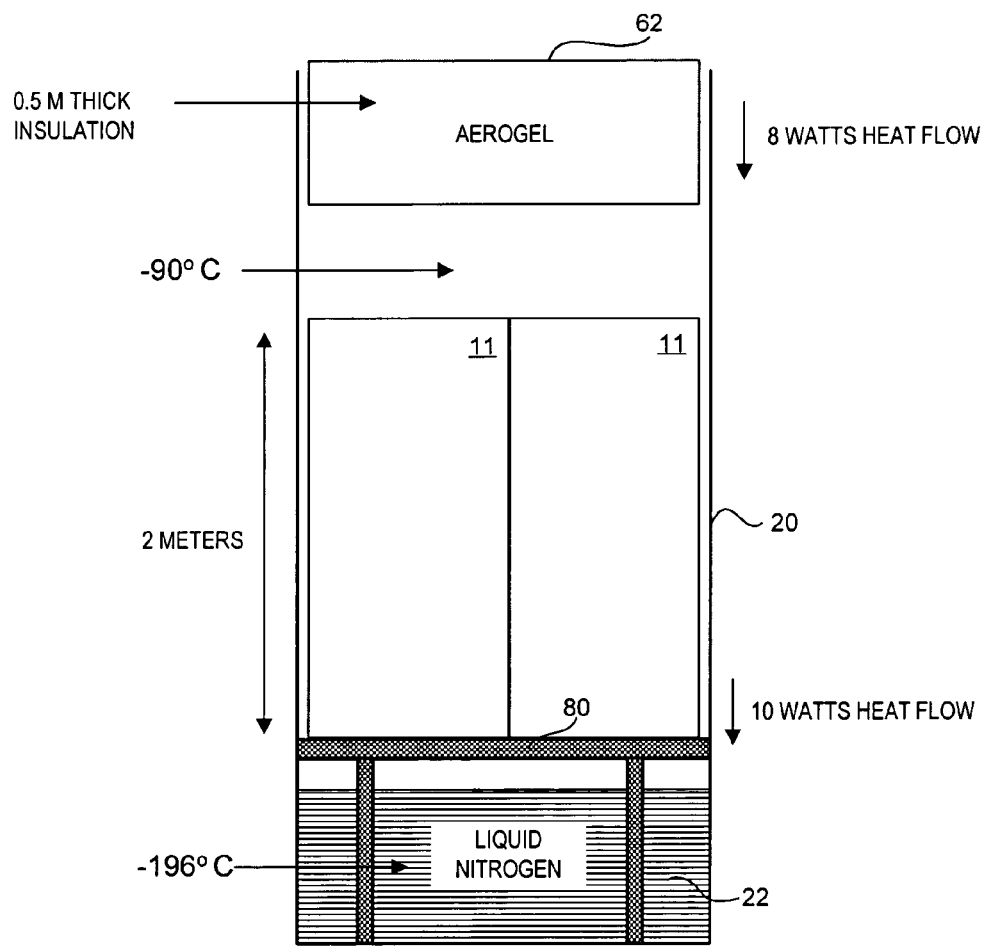
FIG. 14 illustrates an embodiment where three large aerogel-insulated container devices are maintained at an internal temperature near −135° C. in a cryogenic Dewar 20 in liquid nitrogen 22.
Figure 14:
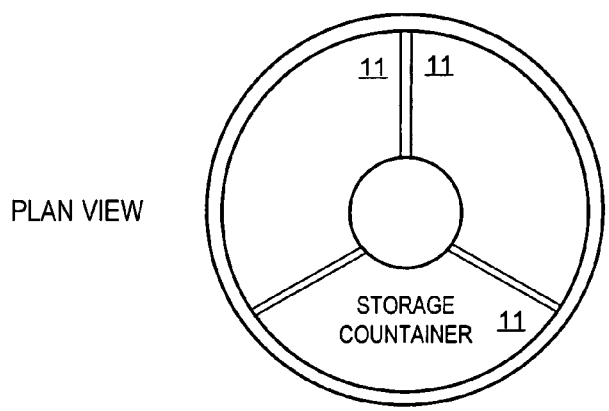

In this example the containers are insulated with 5 cm thick evacuated aerogel having a thermal conductivity k=0.003 W/mK. They are positioned in a Dewar as shown in FIG. 14. The Dewar lid 62 is made of evacuated aerogel, and the containers rest directly on a conductive platform 80 at or near −196° C. No central conductors have been placed in the Dewar, although in some embodiments they are added to increase the efficiency of the system.

Numerical simulation shows that good thermal conductors insulated by 5 cm thick aerogel placed against the 1 mm thick stainless steel of the Dewar inner wall create a composite system with approximately twice the thermal conductivity of the Dewar wall alone. Portions of the Dewar wall in contact with containers are modeled accordingly.

A total of 2 watts of power is added to the final heat flow into the liquid nitrogen. This is consistent with a system where the average temperature surrounding the containers is 5° C. below the target temperature for the temperature chamber.

LN2 consumption is only 5 liters per day. The high efficiency of the aerogel insulation makes it possible for containers to withstand high external temperature gradients without generating unacceptable internal gradients. This removes the need for extra thermal conductors in the Dewar, allowing the Dewar to operate more efficiently.

The performance figures of this example are an upper limit to what might be achieved in a Dewar of this size. Practical implementation details, such as an outer metal skin for the containers (disregarded in this example), would tend to move LN2 consumption closer to 8 liters per day.

Although the Dewar of this example uses an aerogel lid and conductive platform to maximize system performance, aerogel-insulated containers actually require less specialized Dewars for storage than other types of containers. In an emergency, an aerogel-insulated container could even float in the LN2 of an ordinary Dewar with no special platform or other hardware. Only a few watts of heater power are required to maintain a −135° C. internal temperature, even with large proportions of a container submerged under LN2

EXAMPLE 5

Thermodynamic Testing

A prototype of the present invention was built and tested. A commercially-available high density polyethylene (HDPE) 5 gallon beverage cooler was modified by inserting 2" thick disks of foam insulation into the bottom and top of the container interior. This resulted in a total insulation thickness of 2" on top, 1" on the sides, and 3" on the bottom when the insulation that the container is manufactured with is included. The top of the insulation at the bottom of the container was covered with 1/64" sheet aluminum, and dual redundant thermocouples and flat heating elements were affixed to the underside of the aluminum sheet. A removable aluminum can 9¾" wide, 11½" tall, and ⅛" thick was placed inside the cooler, resting on top of the aluminum sheet.

In one test the complete container was placed inside a MVE TA-60 Dewar, and a metal can full of liquid nitrogen was placed on top of the container. This caused the temperature surrounding the container to range from −182° C. at the top to −192° C. at the bottom of the container. 7.5 watts of interior heating power raised the interior temperature to −135° C. The container therefore exhibited a heat leak of 0.15 watts per ° C. interior/exterior temperature difference.

In another test the container was placed inside the TA-60 Dewar with 4" of liquid nitrogen at the bottom, and with the Dewar lid placed on the Dewar in the customary manner. The exterior bottom of the container was therefore at the temperature of LN2 (−196° C.), and the vapor near the top of the container was measured to be at −100° C. After 18 hours, the temperature at the bottom of the aluminum can ("interior conductor") of the container was −152° C., and the temperature at the top of the can was −148° C. The interior temperature of the container was therefore uniform to within 4° C. despite the almost 100° C. vertical temperature difference along the container exterior.

The electronic temperature controller (Omega Industries, Inc., iSeries) was then activated with a set point temperature of −140° C. The 18 watt heater raised the temperature of the aluminum can bottom to −140° C. within 10 minutes. Within 30 minutes the temperature at the top of the aluminum can also reached an equilibrium temperature of −140° C. With the electronic controller operating a single heating element at he bottom interior of the container, the interior reached a temperature that was perfectly uniform within the measurement precision of the instrumentation.

Trial-and-error was used to obtain optimum positioning of the thermocouple temperature probes and heater control algorithm parameters. If the probes were too close to the heating element, they did not accurately reflect the temperature of the aluminum can. If they were too far, the lag time between heater power input and temperature response was too great, creating control difficulties. A PI (proportional-integral) control algorithm was found to be optimum.

EXAMPLE 6

Cryopreserved Cornea Storage and Shipment Device

The device is constructed starting from an R-7 per inch (k=0.02 W/mK) foam cylinder that is 35 cm long and 50 mm in diameter. This fits within the storage space of an MVE sc 4/3 v liquid nitrogen dry shipper. The foam is protected from ingress and egress of liquid nitrogen by bonding aluminum foil to the outer surface. The cylinder is cut transversely into two halves, and a 35 mm wide by 40 mm long compartment is machined into the end of one of the halves. A copper chamber is affixed to the end of the other half such that the aforementioned compartment forms a sleeve that fits over the cooper chamber. This insulating sleeve makes a friction fit, permitting the foam cylinder assembly to be inserted and removed from the dewar. A plastic vial containing the cornea is to be stored within the thermally-uniform and insulated copper chamber.

A thermocouple and a 50 ohm (2 watt) resister is placed in thermal contact with the copper chamber, and connected to a controller outside the dewar with fine gauge wire. An Omega CNi3222-DC controller (12–36 Volts DC, 3 watts) is programmed for PI (proportional/integral) control of a pulse width modulated signal to the resistor sufficient to maintain a target storage temperature of −145° C. Twelve D size batteries (Duracell MN1300) can supply a current of 400 mA (3 watts for controller, 2 watts for resistor heater) for 30 hours before the series voltage drops to 12 volts (the minimum controller supply voltage). This is sufficient time for air shipment of a cryopreserved cornea to anywhere in the world.

EXAMPLE 7

Laboratory Storage Freezer

Figure 15:
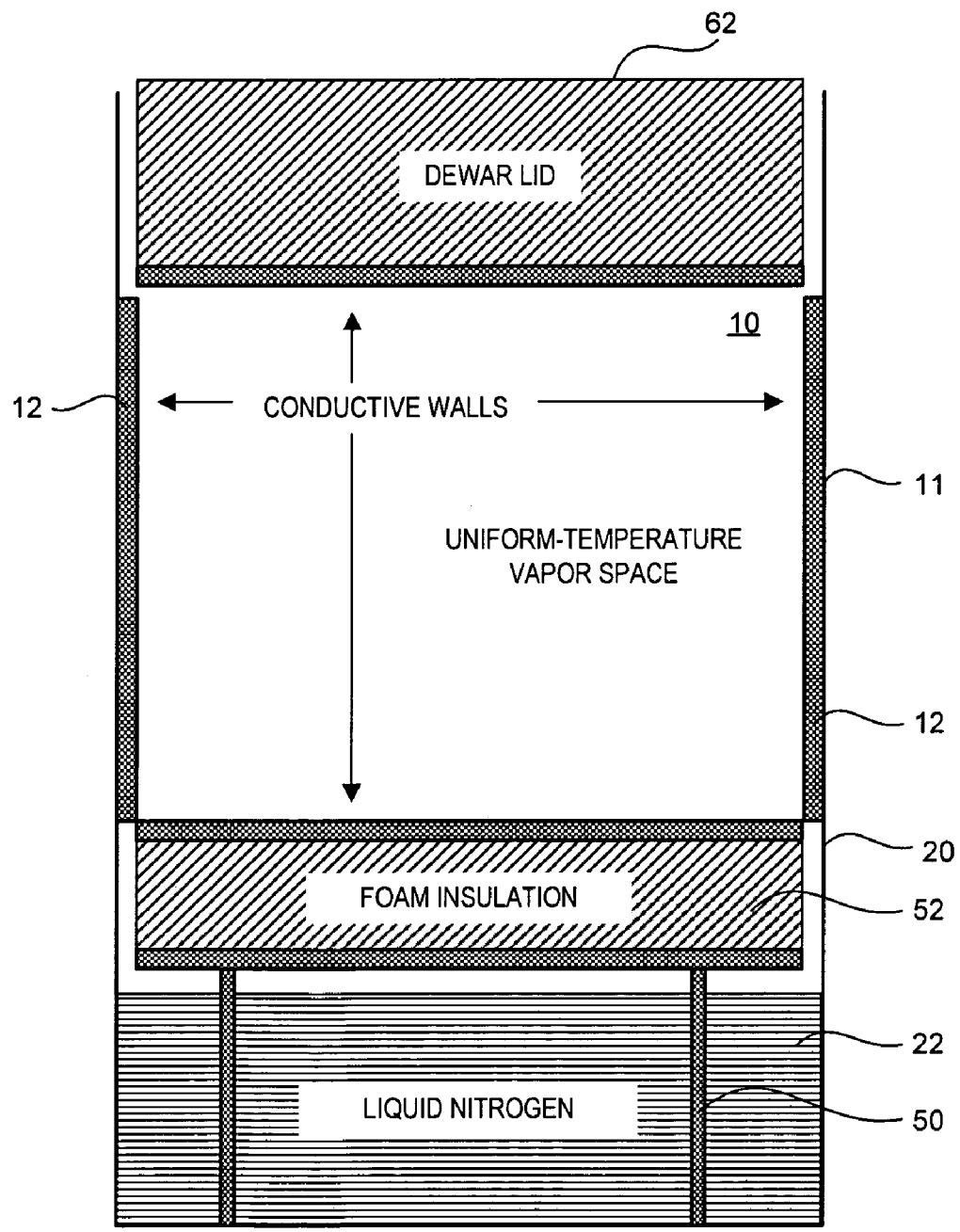
FIG. 15 illustrates a system for establishing a temperature chamber 10 of relatively uniform temperature higher than the temperature of liquid nitrogen 22 within a Dewar 20. In this embodiment the Dewar lid 62, foam insulation 52, and Dewar vacuum insulation (not shown), comprise the thermal insulation of the device.

A Cryomed dewar (MVE 1411 equivalent) 31.75" wide by 34" deep was converted into a −135° C. storage freezer according to the general scheme of FIG. 15. A 7" tall aluminum platform was placed at the bottom of the dewar and covered with 1" thick Johns Manville (R7 per inch) polyisocyanurate foam insulation. A 30.75" outer diameter, 18" tall, aluminum cylinder subdivided into four walled quadrants, and provided with an aluminum floor, was placed on top of this foam insulation. Each storage quadrant was equipped with its own 1.5" thick foam cover with handle, and sheet aluminum on the underside of the cover. (All aluminum parts were made from 0.125" alloy 1100 sheet aluminum.) The standard swing-open lid (7" fiber glass covered foam) of the Cryomed dewar could be opened for easy access to the insulated covers of the storage quadrants.

Additionally, two vertical PVC pipes penetrated the full depth of the storage chamber down into the liquid nitrogen chamber. One pipe provided a path for refilling the liquid nitrogen chamber with liquid nitrogen, and the other pipe incorporated a float for visual monitoring the liquid nitrogen level, and a path for vapor to escape during refilling.

A CNi16D22-EI (Omega iSeries) temperature controller was connected to an Omega KHR-3/2 heater and CO3-T thermocouple placed 1" away from each other on the underside of the storage chamber. A series diode limited the maximum power available to the heating element to 9 watts using AC line voltage. The highest temperature reached by the storage chamber with the heating element in the "full on" state for four days was −129° C. With the heater off, the lowest temperature reached was −145° C. These two temperatures are therefore the upper and lower "fail safe" temperature excursions of the storage unit. The controller can be set to reliably maintain a setpoint temperature anywhere between these two temperatures by sending pulse-width modulated power pulses to the heater using a PI (proportional-integral) control algorithm.

The unit consumed approximately 10 liters of liquid nitrogen per day (85 liter capacity) with an operating setpoint of −135° C. The coldest temperature within the 7.5 cubic foot storage space was −135° C. (bottom), and the warmest temperature was −130° C. (top). The unit was found to be a reliable, quiet, and low-power alternative to mechanical laboratory freezers.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are set forth within the following claims.

The invention claimed is:

1. A device for storing material at a cryogenic temperature, comprising:
   a) a temperature chamber defined by a thermally-conductive container;
   b) at least one layer of thermal insulation surrounding the thermally-conductive container;
   c) one or more heat sources thermally connected to the thermally-conductive container, and
   d) a cold source in thermal contact with (a), (b) and (c) such that heat flows from the temperature chamber to the cold source.

2. The device of claim 1 further comprising a control apparatus for controlling a supply of heat to the thermally-conductive container from the one or more heat sources.

3. The device of claim 1 wherein the thermally-conductive container is comprised of aluminum or copper.

4. The device of claim 1 further comprising at least one temperature sensor that detects the temperature in the temperature chamber.

5. The device of claim 4 wherein two or more temperature sensors detect the temperature at two or more distinct locations on or within the thermally-conductive container.

6. The device of claim 2 wherein the control apparatus causes heat to be supplied by at least one heat source located on or within the thermally conductive container or within the temperature chamber to maintain a set temperature.

7. The device of claim 1 wherein two or more heat sources are thermally connected to two or more distinct locations on or within the thermally conductive container and supply heat to the distinct locations to maintain a uniform temperature in the temperature chamber.

8. The device of claim 7 wherein the two or more heat sources are thermally and electrically connected to the thermally conductive container.

9. The device of claim 1 wherein the cold source is a cold liquid, solid or gas in contact with the insulation that surrounds the thermally-conductive container.

10. The device of claim 9 wherein the cold source is a cold environment into which the thermally-conductive container and its surrounding insulation may be inserted and removed.

11. The device of claim 9 wherein the cold liquid, solid or gas is inside a cryogenic Dewar.

12. The device of claim 10 wherein the cold environment is the interior of a cryogenic Dewar.

13. The device of claim 1 wherein thermal insulation is selected from the group consisting of: aerogel, perlite, vermiculite, polyurethane, polystyrene, glass fiber, cellulose fiber, polyester fiber, polyethylene, polyurethane, polystyrene, polyisocyanurate, high vacuum insulation, and polyisocyanurate.

14. The device of claim 9 wherein the cold source is in a Dewar containing liquid nitrogen and the temperature of the thermally-conductive container is −135° C.±5° C.

15. The device of claim 10 wherein die temperature chamber is maintained at a temperature of 0° C.±4° C.

16. Three or more devices of claim 1 located inside a cold source.

17. A method for storing biological material at a cryogenic temperature, comprising:
placing biological material to be stored at a cryogenic temperature in a device comprising
a) a temperature chamber defined by a thermally-conductive container;
b) at least one layer of thermal insulation surrounding the thermally-conductive container;
c) one or more heat sources thermally connected to die thermally-conductive container; and
d) a cold source in thermal contact with (a), (b) and (c) such that heat flows from the temperature chamber to the cold source; and
maintaining the temperature chamber at a cryogenic temperature.

18. The method of claim 17 wherein the device further comprises a control apparatus for controlling and regulating the supply of heat to the thermally-conductive container from the one or more heat sources.

19. The method of claim 17 wherein the thermally-conductive container is comprised of aluminum or copper.

20. The method of claim 18 wherein the device further comprises at least one temperature sensor that detects the temperature in the temperature chamber.

21. The method of claim 20 wherein the device further comprises two or more temperature sensors that detect the temperature at two or more distinct locations on or within the thermally-conductive container.

22. The method of claim 21 wherein the control device causes heat to be supplied by at least one heat source located on or within the thermally conductive container or within the temperature chamber to maintain a set temperature.

23. The method of claim 17 wherein the device further comprises two or more heat sources thermally connected to two or more distinct locations on or within the thermally conductive container, and wherein the heat sources supply heat to the distinct locations as required to maintain a uniform temperature in the temperature chamber.

24. The method of claim 17 wherein the cold source is a cold liquid, solid or gas in contact with the insulation that surrounds the thermally-conductive container.

25. The method of claim 24 wherein the temperature chamber is maintained at a temperature of −135° C.±5° C.

26. The method of claim 24 wherein the temperature chamber is maintained at a temperature of 0° C.±4° C.

27. The method of claim 24 wherein the cold source is a cold environment into which the thermally-conductive container and its surrounding insulation may be inserted and removed.

28. The method of claim 24 wherein the cold source is a cryogenic Dewar.

29. The method of claim 24 wherein the cold source is a mechanical refrigerator or freezer.

30. The method of claim 28 wherein the device is maintained within a layer of liquid nitrogen vapor within the cryogenic Dewar.

31. The method of claim 17 wherein thermal insulation is selected from the group consisting of aerogel, perlite, vermiculite, polyurethane, polystyrene, glass fiber, cellulose fiber, polyester fiber, polyethylene, polyurethane, polystyrene, high vacuum insulation, and polyisocyanurate.

32. The method of claim 17 wherein the biological material is selected from the group consisting of: biological tissues, organs, and biological cells.

* * * * *